United States Patent
Higgins et al.

(10) Patent No.: US 9,119,829 B2
(45) Date of Patent: Sep. 1, 2015

(54) METHODS AND COMPOSITIONS FOR DELIVERING INTERLEUKIN-1 RECEPTOR ANTAGONIST

(71) Applicant: Biomet Biologics, LLC., Warsaw, IN (US)

(72) Inventors: Joel Higgins, Claypool, IN (US); Jacy Hoeppner, Warsaw, IN (US); Jennifer Woodell-May, Warsaw, IN (US)

(73) Assignee: Biomet Biologics, LLC, Warsaw, IN (US)

( * ) Notice: Subject to any disclaimer, the term of this patent is extended or adjusted under 35 U.S.C. 154(b) by 0 days.

(21) Appl. No.: 13/782,421

(22) Filed: Mar. 1, 2013

(65) Prior Publication Data

US 2013/0178425 A1    Jul. 11, 2013

Related U.S. Application Data

(63) Continuation of application No. PCT/US2011/048909, filed on Aug. 24, 2011.

(60) Provisional application No. 61/380,026, filed on Sep. 3, 2010.

(51) Int. Cl.
| | |
|---|---|
| *A61K 38/19* | (2006.01) |
| *A61K 38/21* | (2006.01) |
| *A61K 38/20* | (2006.01) |
| *A61K 35/15* | (2015.01) |
| *A61K 38/17* | (2006.01) |
| *A61K 38/18* | (2006.01) |

(52) U.S. Cl.
CPC ............... *A61K 38/217* (2013.01); *A61K 35/15* (2013.01); *A61K 38/177* (2013.01); *A61K 38/1793* (2013.01); *A61K 38/1825* (2013.01); *A61K 38/1841* (2013.01); *A61K 38/191* (2013.01); *A61K 38/2006* (2013.01); *A61K 38/2026* (2013.01); *A61K 38/2066* (2013.01); *A61K 38/2073* (2013.01); *A61K 38/2086* (2013.01)

(58) Field of Classification Search
None
See application file for complete search history.

(56) References Cited

U.S. PATENT DOCUMENTS

| | | |
|---|---|---|
| 4,853,137 A | 8/1989 | Ersson |
| 5,075,222 A | 12/1991 | Hannum et al. |
| 5,165,938 A | 11/1992 | Knighton |
| 5,571,418 A | 11/1996 | Lee et al. |
| 5,585,007 A | 12/1996 | Antanavich et al. |
| 5,599,558 A | 2/1997 | Gordinier et al. |
| 5,641,622 A | 6/1997 | Lake et al. |
| 5,788,662 A | 8/1998 | Antanavich et al. |
| 5,830,359 A | 11/1998 | Knight et al. |
| 5,895,575 A | 4/1999 | Kraus et al. |
| 5,916,743 A | 6/1999 | Lake et al. |
| 6,063,297 A | 5/2000 | Antanavich et al. |
| 6,096,728 A | 8/2000 | Collins et al. |
| 6,214,338 B1 | 4/2001 | Antanavich et al. |
| 6,287,558 B1 | 9/2001 | Lanza et al. |
| 6,398,972 B1 | 6/2002 | Blasetti et al. |
| 6,599,873 B1 | 7/2003 | Sommer et al. |
| 6,623,472 B1 | 9/2003 | Reincke et al. |
| 6,645,388 B2 | 11/2003 | Sheikh-Ali et al. |
| 6,649,072 B2 | 11/2003 | Brandt et al. |
| 6,713,246 B1 | 3/2004 | Reinecke et al. |
| 6,759,188 B2 | 7/2004 | Reinecke et al. |
| 6,790,371 B2 | 9/2004 | Dolecek |
| 6,905,612 B2 | 6/2005 | Dorian et al. |
| 6,955,642 B1 | 10/2005 | Simon |
| 7,011,852 B2 | 3/2006 | Sukavaneshvar et al. |
| 7,148,209 B2 | 12/2006 | Hoemann et al. |
| 7,179,391 B2 | 2/2007 | Leach et al. |
| 7,223,346 B2 | 5/2007 | Dorian et al. |
| 7,374,678 B2 | 5/2008 | Leach et al. |
| 7,465,293 B2 | 12/2008 | Reinecke et al. |
| 7,470,371 B2 | 12/2008 | Dorian et al. |
| 7,520,849 B1 | 4/2009 | Simon |
| 7,553,413 B2 | 6/2009 | Dorian et al. |
| 7,608,258 B2 | 10/2009 | Mishra |
| 7,708,152 B2 | 5/2010 | Dorian et al. |
| 7,901,344 B2 | 3/2011 | Yoo |

(Continued)

FOREIGN PATENT DOCUMENTS

| | | |
|---|---|---|
| EP | 0417818 | 3/1991 |
| EP | 2186877 | 5/2010 |

(Continued)

OTHER PUBLICATIONS

PLASMAX brochure, downloaded from http://www.biomet.com/biologics/information/pdf/BBI0020.0_061508.pdf on Jun. 12, 2014.*

(Continued)

*Primary Examiner* — Brian J Gangle
*Assistant Examiner* — Andrea McCollum
(74) *Attorney, Agent, or Firm* — Schwegman Lundberg & Woessner, P.A.

(57) ABSTRACT

Methods, systems, and compositions related to generating and using a solution rich in interleukin-1 receptor antagonist are provided. Methods include contacting a liquid comprising white blood cells with a solid extraction material and stimulating with an electromagnetic field to activate production of interleukin-1 receptor antagonist. The interleukin-1 receptor antagonist can be separated from the solid extraction material. Methods for treating a site of inflammation in a patient include administering the solution rich in interleukin-1 receptor antagonist to the site of inflammation.

3 Claims, 13 Drawing Sheets

(56) References Cited

U.S. PATENT DOCUMENTS

| | | | |
|---|---|---|---|
| 7,914,689 | B2 | 3/2011 | Higgins et al. |
| 8,048,321 | B2 | 11/2011 | Leach et al. |
| 2001/0009757 | A1 | 7/2001 | Bischof et al. |
| 2001/0053764 | A1 | 12/2001 | Sims et al. |
| 2002/0077276 | A1* | 6/2002 | Fredeking et al. ............... 514/2 |
| 2003/0091536 | A1 | 5/2003 | Frisbie et al. |
| 2003/0138910 | A1 | 7/2003 | Reinecke et al. |
| 2003/0194397 | A1 | 10/2003 | Mishra |
| 2003/0198687 | A1 | 10/2003 | Bennett et al. |
| 2003/0205538 | A1 | 11/2003 | Dorian et al. |
| 2004/0120942 | A1 | 6/2004 | McGinnis et al. |
| 2004/0156823 | A1 | 8/2004 | Reinecke et al. |
| 2004/0182788 | A1 | 9/2004 | Dorian et al. |
| 2004/0182795 | A1 | 9/2004 | Dorian et al. |
| 2004/0251217 | A1 | 12/2004 | Leach et al. |
| 2005/0049640 | A1 | 3/2005 | Gurtner et al. |
| 2005/0084962 | A1 | 4/2005 | Simon |
| 2005/0109716 | A1 | 5/2005 | Leach et al. |
| 2005/0130301 | A1 | 6/2005 | McKay et al. |
| 2005/0186120 | A1 | 8/2005 | Dorian et al. |
| 2005/0186193 | A1 | 8/2005 | Mishra |
| 2005/0196874 | A1 | 9/2005 | Dorian et al. |
| 2005/0197293 | A1 | 9/2005 | Mellis et al. |
| 2005/0271738 | A1 | 12/2005 | Simon |
| 2006/0051865 | A1 | 3/2006 | Higgins et al. |
| 2006/0057223 | A1 | 3/2006 | DiMauro et al. |
| 2006/0057693 | A1 | 3/2006 | Simon |
| 2006/0175244 | A1 | 8/2006 | Dorian et al. |
| 2006/0243676 | A1 | 11/2006 | Swift et al. |
| 2006/0273049 | A1 | 12/2006 | Leach et al. |
| 2006/0278588 | A1 | 12/2006 | Woodell-May |
| 2007/0075016 | A1 | 4/2007 | Leach |
| 2007/0105769 | A1 | 5/2007 | Simon |
| 2007/0207161 | A1 | 9/2007 | Ralph |
| 2007/0208321 | A1 | 9/2007 | Leach et al. |
| 2007/0299472 | A1 | 12/2007 | Brighton |
| 2008/0011684 | A1 | 1/2008 | Dorian et al. |
| 2008/0044852 | A1 | 2/2008 | Kanayinkal et al. |
| 2008/0064626 | A1 | 3/2008 | Zanella |
| 2008/0193424 | A1 | 8/2008 | McKale et al. |
| 2008/0217263 | A1* | 9/2008 | Higgins et al. ............... 210/787 |
| 2008/0268064 | A1 | 10/2008 | Woodell-May |
| 2008/0269762 | A1 | 10/2008 | Simon et al. |
| 2008/0283474 | A1 | 11/2008 | Leach et al. |
| 2009/0014391 | A1 | 1/2009 | Leach et al. |
| 2009/0047242 | A1 | 2/2009 | Reinecke et al. |
| 2009/0101599 | A1 | 4/2009 | Dorian et al. |
| 2009/0112146 | A1 | 4/2009 | Wratten et al. |
| 2009/0181019 | A1 | 7/2009 | Solinger |
| 2009/0192528 | A1 | 7/2009 | Higgins et al. |
| 2009/0220482 | A1* | 9/2009 | Higgins et al. ............. 424/94.64 |
| 2009/0221075 | A1 | 9/2009 | Dorian et al. |
| 2009/0236297 | A1 | 9/2009 | Dorian et al. |
| 2009/0250413 | A1 | 10/2009 | Hoeppner |
| 2009/0253566 | A1 | 10/2009 | Chavarria |
| 2009/0317439 | A1 | 12/2009 | Turzi et al. |
| 2010/0008992 | A1 | 1/2010 | Ichim |
| 2010/0015129 | A1 | 1/2010 | Abramson et al. |
| 2010/0055087 | A1* | 3/2010 | Higgins et al. ............. 424/94.64 |
| 2010/0125236 | A1 | 5/2010 | Bare et al. |
| 2010/0140182 | A1 | 6/2010 | Chapman et al. |
| 2011/0052561 | A1 | 3/2011 | Hoeppner |
| 2011/0059082 | A1 | 3/2011 | Germer et al. |
| 2011/0059083 | A1 | 3/2011 | Aigner et al. |
| 2011/0059084 | A1 | 3/2011 | Osterroth et al. |
| 2011/0129441 | A1 | 6/2011 | Lentz |
| 2011/0189172 | A1 | 8/2011 | Solinger et al. |
| 2011/0268708 | A1 | 11/2011 | Lin et al. |
| 2012/0027746 | A1 | 2/2012 | Dorian et al. |
| 2012/0093936 | A1 | 4/2012 | Lindenberg et al. |
| 2012/0172836 | A1 | 7/2012 | Higgins et al. |

FOREIGN PATENT DOCUMENTS

| | | |
|---|---|---|
| JP | H1045616 A | 2/1998 |
| WO | WO 99/67277 | 12/1999 |
| WO | WO 2004/009207 | 1/2004 |
| WO | WO 2007/121538 | 11/2007 |
| WO | WO 2007/128973 | 11/2007 |
| WO | WO 2008/100442 | 8/2008 |
| WO | 2008/157733 A2 | 12/2008 |
| WO | WO 2009/108890 | 9/2009 |
| WO | WO 2011/031524 | 3/2011 |
| WO | WO 2011/031553 | 3/2011 |
| WO | WO 2012/030593 | 3/2012 |

OTHER PUBLICATIONS

Aaron et al., "Acceleration of Experimental Endochondral Ossification by Biophysical Stimulation of the Progenitor Cell Pool", Journal of Orthopaedic Research, vol. 14, No. 4, 1996, pp. 582-589.

Aaron et al., "Power Frequency Fields Promote Cell Differentiation Coincident With an Increase in Transforming Growth Factor-β1 Expression", Bioelectromagnetics, vol. 20, 1999, pp. 453-458.

Aaron et al., "Stimulation of Experimental Endochondral Ossification by Low-Energy Pulsing Electromagnetic Fields", Journal of Bone and Mineral Research, vol. 4, No. 2, 1989, pp. 227-233.

Aaron et al., "Therapeutic Effects of Electromagnetic Fields in the Stimulation of Connective Tissue Repair", Journal of Cellular Biochemistry, vol. 52, 1993, pp. 42-46.

Aaron et al., "Upregulation of basal TGFβ1 levels by EMF coincident with chondrogenesis—implications for skeletal repair and tissue engineering", Journal of Orthopaedic Research, vol. 20, 2002, pp. 233-240.

Arend, W. et al. "Interleukin-1 Receptor Antagonist: Role in Biology" Annu. Rev. Immunol., vol. 16 (pp. 27-55) 1998.

Bendele et al. "Combination benefit of treatment with the cytokine inhibitors interleukin-1 receptor antagonist and PEGylated soluble tumor necrosis factor receptor type I in animal models of rheumatoid arthritis" Arthritis & Rheumatism, vol. 43, No. 12, Dec. 2000, pp. 2648-2659.

Biomet Biologics, Inc. "GPS® III Platelet Separation System" Product Brochure (8 pages) 2007.

Biomet Biologics, Inc. "Plasmax Plasma Concentrate" Brochure (2006) 5 pages.

Biomet Biologics, Inc. "GPS System Shoulder Recovery with the GPS Platelet Concentrate System" Product Brochure (6 pages) 2004.

Burnouf, T. "Blood-derived, tissue engineering biomaterials" Biomedical Engineering-Applications, Basis & Communications, vol. 16, No. 6, Dec. 2004 (pp. 294-304).

Cell Factor Technologies, Inc. "GPS® Platelet Concentrate System" Product Brochure (9 pages) 2004.

Cell Factor Technologies, Inc. "Gravitational Platelet Separation System" User Manual (2005) 13 pages.

Dinarello, C. "Interleukin-1 and Interleukin-1 Antagonism" Blood, vol. 77, No. 8 (pp. 1627-1652) Apr. 1991.

Juge-Aubry, C. et al. "Adipose Tissue is a Major Source of Interleukin-1 Receptor Antagonist" Diabetes, vol. 52, May 2004 (pp. 1104-1110).

Kaufman, A. et al. "Human macrophage response to UHMWPE, TiAlV, CoCr, and alumina particles: Analysis of multiple cytokines using protein arrays" Journal of Biomedical Materials Research Part A, published online in Wiley InterScience DOI: 10.1002/jbm.a. 31467 (pp. 464-474) Jul. 2007.

Kim, Seon Hee et al. "Ex vivo gene delivery of Il-1Ra and soluble TNF receptor confers a distal synergistic therapeutic effect in antigen-induced arthritis", Molecular Therapy, vol. 6, No. 5, Nov. 1, 2002 (pp. 591-600).

Lavi, Galia; et al; "Sustained delivery of IL-1Ra from biodegradable microspheres reduces the number of murine B16 melanoma lung metastases" Journal of Controlled Release, 123, 123-130, 2007.

Matthews, J. et al. "Comparison of the response of primary human peripheral blood mononuclear phagocytes from different donors to challenge with model polyethylene particles of known size and dose" Biomaterials, vol. 21 (pp. 2033-2044) 2000.

(56) References Cited

OTHER PUBLICATIONS

Meijer, H. et al. "The Production of Anti-Inflammatory Cytokines in whole Blood by physico-chemical induction" Inflamm. Res., vol. 52 (pp. 404-407) Oct. 2003.

Muzio, M. et al. "Interleukin-13 Induces the Production of Interleukin-1 Receptor Antagonist (IL-1ra) and the Expression of the mRNA for the Intracellular (Keratinocyte) Form of IL-1ra in Human Myelomonocytic Cells" Blood, vol. 83, No. 7 (pp. 1738-1743) Apr. 1994.

Plasmax® Plasma Concentration System. 2007. Biomet Biologics. p. 1-20.

Rader, C. et al. "Cytokine Response of Human Macrophage-like Cells After Contact With Polyethylene and Pure Titanium Particles" The Journal of Arthroplasty, vol. 14, No. 7 (pp. 840-848 (Oct. 1999).

Swift, M. et al. "Characterization of Growth Factors in Platelet Rich Plasma" Cell Factor Technologies, Inc. Printed Sep. 16, 2005 from www.cellfactortech.com/global_products.cfm.

Vangsness, T. et al. "Stimulation of IL-1ra Production from Platelet-Rich Plasma" Poster No. 488 presented at 54th Annual Meeting of the Orthopeadic Research Society in San Francisco, CA (1 page) Mar. 2-5, 2008.

Woodell-May "Autologous Protein Solution Inhibits MMP-13 Production by IL-1 and TNF . . . " J. of Ortho Research vol. 29, No. 9, Mar. 15, 2011.

Woodell-May, J. et al. "Effect of Incubation Time on Production of IL-1ra and sTNF-RI from Platelet-Rich Plasma" Paper No. 200, 55th Annual Meeting of the Orthopaedic Research Society (1 page) Feb. 2009.

Woodell-May, J. et al. "Elution of IL-1ra from a concentrated-plasma matrix—An in vitro study" Poster Presentation at 8th World Congress of the International Cartilage Repair Society, Miami, FL. (1 page) May 2009.

Wright-Carpenter, T. "Treatment of Muscle Injuries by Local Administration of Autologous Conditioned Serum: A Pilot Study on Sportsmen with Muscle Strains" Int J Sports Med, vol. 25 (pp. 588-593) Oct. 2004.

Yang, S. et al. "Protective effects of IL-1Ra or vIL-10 gene transfer on a murine model of wear debris-induced osteolysis" Gene Therapy, vol. 11 (pp. 483-491) 2004.

Yang, T. et al. "Recent Applications of Polyacrylamide as Biomaterials" Recent Patents on Materials Science, vol. 1 (pp. 29-40) 2008.

Dinarello, C. A. Interleukin-1 in the pathogenesis and treatment of inflammatory diseases. Blood, 2011, vol. 117 (14), p. 3720-3732.

\* cited by examiner

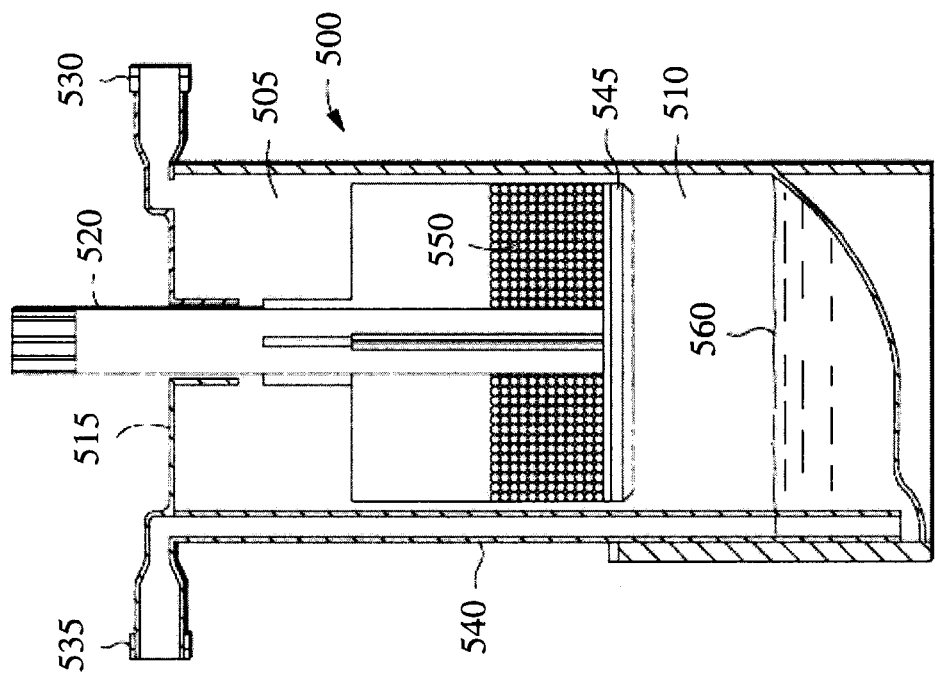
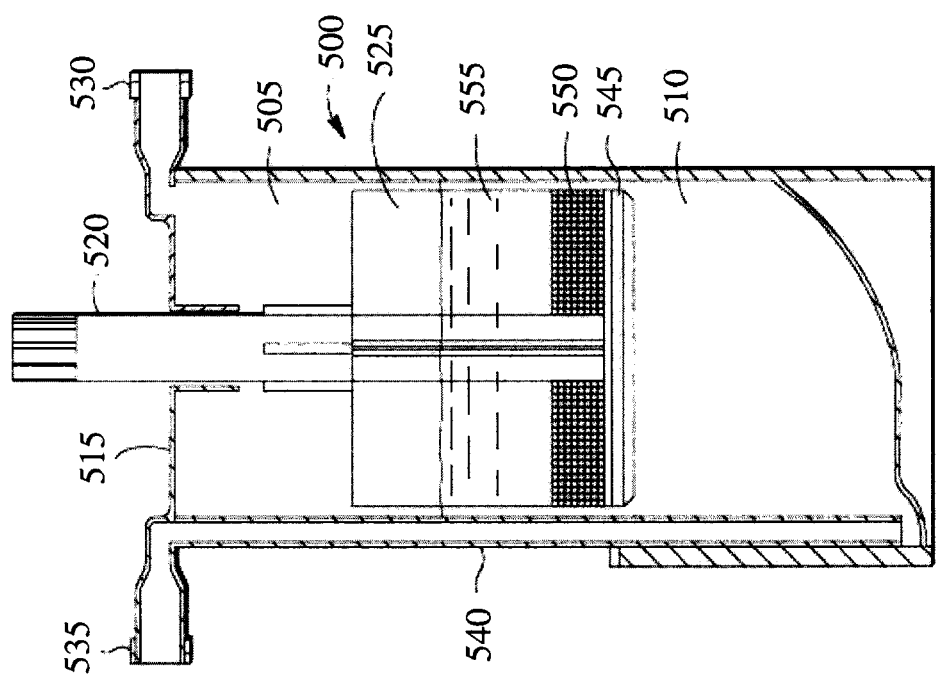
Fig. 5A
Fig. 5B

METHODS AND COMPOSITIONS FOR DELIVERING INTERLEUKIN-1 RECEPTOR ANTAGONIST

CROSS-REFERENCE TO RELATED APPLICATIONS

This application is a continuation of International Application No. PCT/US2011/048909, filed Aug. 24, 2011, which claims the benefit of U.S. Provisional Application No. 61/380,026, filed on Sep. 3, 2010. The entire disclosures of each of the above applications are incorporated herein by reference.

The present technology relates to compositions comprising interleukin-1 receptor antagonist, and methods for generating, isolating, and administering such compositions.

Interleukin-1 (IL-1) includes a family of cytokines that can stimulate lymphocytes and macrophages, activate phagocytes, increase prostaglandin production, contribute to degeneration of bone joints, increase bone marrow cell proliferation, and are involved in many chronic inflammatory conditions. IL-1 can be generated by macrophages, monocytes, and dendritic cells, and can be part of the inflammatory response against infection.

The mode of action of IL-1 can be mediated by interleukin-1 receptor antagonist protein (IL-1ra; also known as "IRAP"). IL-1ra binds to the same receptor on the cell surface as IL-1, and thus prevents IL-1 from sending a signal to that cell. IL-1ra is secreted from white blood cells, including monocytes, macrophages, neutrophils, polymorphonuclear cells (PMNs), and other cells, and can modulate a variety of IL-1 related immune and inflammatory responses, as described by Arend W P, Malyak M, Guthridge C J, Gabay C (1998) "Interleukin-1 receptor antagonist: role in biology" Annu. Rev. Immunol. 16: 27-55. Production of IL-1ra is stimulated by several substances including adherent immunoglobulin G (IgG), other cytokines, and bacterial or viral components. IL-1ra is an important natural anti-inflammatory protein in arthritis, colitis, and granulomatous pulmonary disease.

IL-1ra can be used in the treatment of rheumatoid arthritis, an autoimmune disease in which IL-1 plays a key role, reducing inflammation and cartilage degradation associated with the disease. For example, Kineret™ (anakinra) is a recombinant, non-glycosylated form of IL-1ra (Amgen Manufacturing, Ltd., Thousand Oaks, Calif.). Various recombinant interleukin-1 inhibitors and methods of treatment are described in U.S. Pat. No. 6,599,873, Sommer et al., issued Jul. 29, 2003; U.S. Pat. No. 5,075,222, Hannum et al., issued Dec. 24, 1991; and U.S. Patent Application Publication No. 2005/0197293, Mellis et al., published Sep. 8, 2005 In addition, methods for producing IL-1ra from body fluids, including the use of autologous fluids, are described in U.S. Pat. No. 6,623,472, Reincke et al., issued Sep. 23, 2003; U.S. Pat. No. 6,713,246, Reinecke et al., issued Mar. 30, 2004; and U.S. Pat. No. 6,759,188, Reinecke et al., issued Jul. 6, 2004.

Compositions and methods using IL-1ra are known in the art. For example, IL-1ra has been delivered as part of a composition with hyaluronic acid, as described in U.S. Pat. No. 6,096,728, Collins et al., issued Aug. 1, 2000. However, many such methods and compositions are associated with issues regarding stability and half-life of IL-1ra as well as the amount and rate of IL-1ra provided. Accordingly, improved compositions and methods of delivering IL-1ra are desirable and would be useful in treating conditions and pathologies mediated by the interleukin-1 receptor, including the management of inflammation.

SUMMARY

The present technology provides compositions, apparatus, and methods relating to interleukin-1 receptor antagonist, generating interleukin-1 receptor antagonist, and administering interleukin-1 receptor antagonist to a patient to treat a condition mediated by the interleukin-1 receptor, such as inflammation.

Methods for generating interleukin-1 receptor antagonist include contacting a liquid comprising white blood cells with a solid extraction material. The liquid can be whole blood, bone marrow aspirate, adipose tissue, fractions thereof (e.g., platelet-rich plasma), and mixtures thereof. The solid extraction material can comprise materials such as glasses, minerals, polymers, metals, or polysaccharides, where these materials can be in the form of beads, fibers, powder, and/or porous materials. The contacting can include incubating the liquid with the solid extraction material for a period of time of from about 30 seconds to about 24 hours. A solution can then be separated from the solid extraction material where the concentration of interleukin-1 receptor antagonist in the solution is greater than the concentration of interleukin-1 receptor antagonist in the liquid prior to the contacting step.

Methods for generating interleukin-1 receptor antagonist further include contacting a liquid comprising white blood cells with a solid extraction material, and subjecting the liquid to an electromagnetic field. A solution comprising interleukin-1 receptor antagonist is then separated from the solid extraction material. The combination of contact with the solid extraction material and subjecting the liquid to the electromagnetic field can cause the white blood cells to generate more interleukin-1 receptor antagonist or to generate interleukin-1 receptor antagonist faster than either step applied alone. For example, the combined effect can produce about the same amount of interleukin-1 receptor antagonist in several minutes, up to about an hour, as is produced when the liquid comprising white blood cells is contacted with the solid extraction material for up to 24 hours without being subjected to the electromagnetic field. A pulsed electromagnetic field or a capacitively coupled electromagnetic field can be used. The resulting concentration of interleukin-1 receptor antagonist in the solution is greater than the concentration of interleukin-1 receptor antagonist in the liquid prior to the contacting.

Various ways to prepare a liquid comprising white blood cells are provided. Some methods include centrifuging a tissue, such as blood, to increase the concentration of white blood cells and platelets relative to whole blood. Such methods include those where the tissue is loaded into a tube comprising a buoy disposed in the tube, wherein the buoy has a density such that the buoy is operable to reach an equilibrium position upon centrifugation of the tissue in the tube, the position being between a white blood cell fraction and a second fraction, wherein the white blood cell fraction has a concentration of white blood cells greater than the concentration of white blood cells in the second fraction. Other methods include mixing a tissue or tissue fraction comprising white blood cells with magnetic beads that are coupled to an antibody operable to bind mononuclear leukocytes. The mononuclear leukocytes bound by the antibody are then collected for use as the liquid comprising concentrated white blood cells. And other methods include passing a tissue or tissue fraction comprising white blood cells through a size exclusion filter.

Outputs of the present methods provide compositions and solutions of interleukin-1 receptor antagonist. Solutions of interleukin-1 receptor antagonist can include interleukin-1 receptor antagonist (e.g., at least about 30,000 pg/mL), soluble tumor necrosis factor receptor, viable white blood cells, and/or growth factors. For example, the total concentration of plasma proteins in the solution can be at least about 80 mg/mL.

Methods of treating inflammation in a human or animal subject are provided that include administering to the site of inflammation a solution of interleukin-1 receptor antagonist, where the solution is made using the present methods. For example, treatment methods can be used for inflammation, such as osteolysis associated with wear debris at the site of an artificial joint implant in a human or animal subject, or where the inflammation is associated with osteoarthritis.

BRIEF DESCRIPTION OF THE DRAWINGS

FIGS. 5A and 5B are cross-sectional views of a representative device for incubating a volume of white blood cells with polyacrylamide beads according to one embodiment of the present technology.

It should be noted that the figures set forth herein are intended to exemplify the general characteristics of materials, devices, and methods among those of the present technology, for the purpose of the description of certain embodiments. These figures may not precisely reflect the characteristics of any given embodiment, and are not necessarily intended to fully define or limit specific embodiments within the scope of this technology.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. A non-limiting discussion of terms and phrases intended to aid understanding of the present technology is provided at the end of this Detailed Description.

Figure 1:
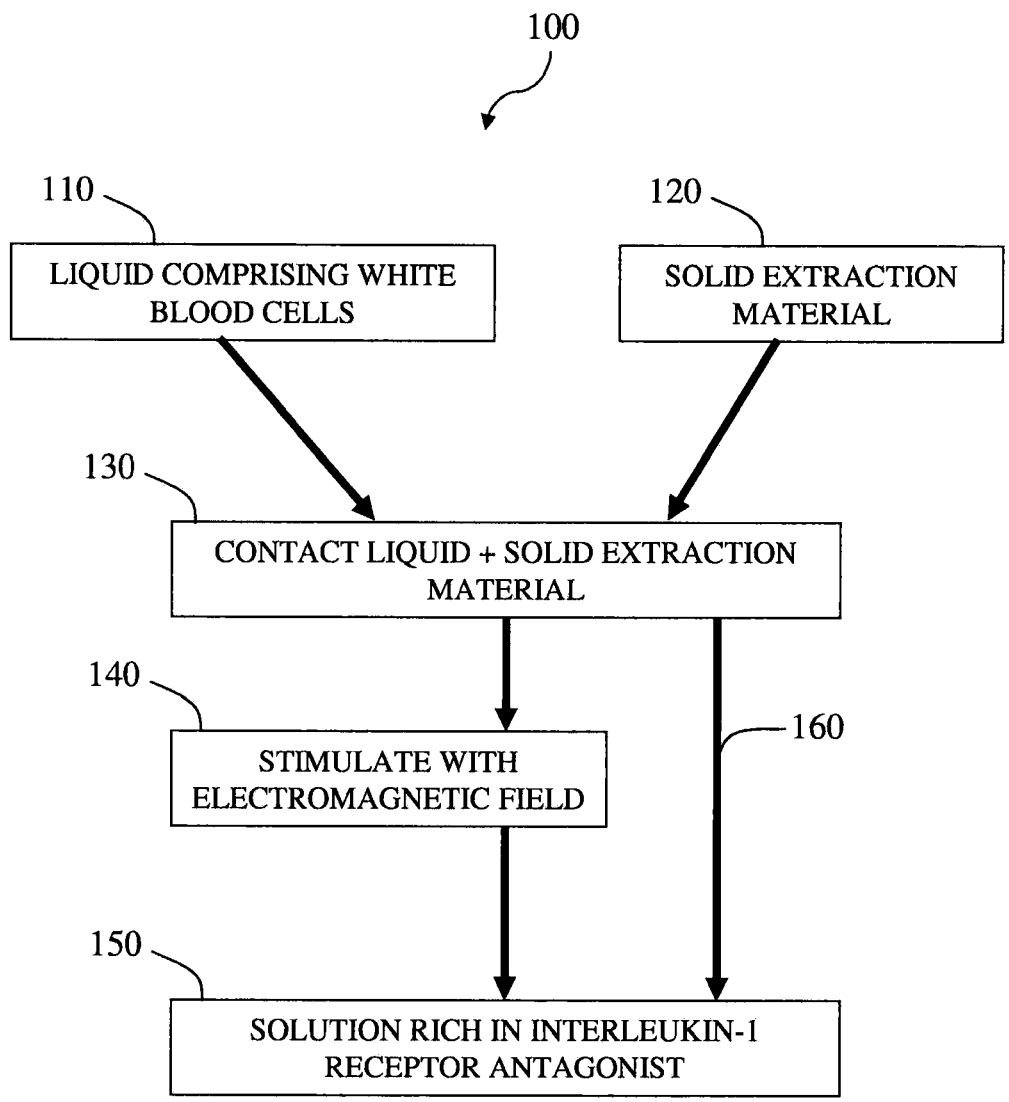
FIG. 1 is a diagrammatic illustration of a method to generate a solution rich in IL-1ra according to an embodiment of the present technology.

The present technology relates to compositions, apparatus, and methods that generate, use, and include interleukin-1 receptor antagonist (IL-1ra). With reference to FIG. 1, a method 100 for generating a solution rich in interleukin-1 receptor antagonist is shown in diagrammatic fashion. A liquid volume comprising white blood cells 110 and a solid extraction material 120 are contacted as shown at 130. An electromagnetic field is used to stimulate the cells as shown at 140. The contacting 130 and stimulating 140 result in a solution rich in IL-1ra, as depicted at 150. In some embodiments, however, the liquid comprising white blood cells is not stimulated or subjected to the electromagnetic field; i.e., step 140 is omitted. Where the liquid comprising white blood cells is not subjected to an electromagnetic field, step 130 proceeds directly to step 150, as shown by arrow 160. The IL-1ra rich solution at 150 can be used to treat inflammation. By rich in IL-1ra, it is meant that the solution comprises a greater amount of IL-1ra than found in an equivalent volume of whole blood.

Contacting 140 the liquid comprising white blood cells 110 with the solid extraction material 120 in conjunction with the electromagnetic field stimulation 140 can generate IL-1ra more rapidly and/or can generate a greater amount of IL-1ra than performing the contacting 130 or stimulating 140 alone. For example, exposing the liquid comprising white blood cells to the electromagnetic field can accelerate the rate of protein production that follows contact of the white blood cells with the solid extraction material. In some cases, the present methods can provide a solution rich in IL-1ra in less than 1 hour where other methods to generate IL-1ra can take from about 4 to about 24 hours to generate an equivalent amount. Referring again to FIG. 1, the method including steps 130 and 140 can generate IL-1ra at a faster rate and/or can generate more IL-1ra than the method that bypasses step 140 as shown by arrow 160.

Accordingly, the present methods can afford faster and/or greater production of IL-1ra compared to other methods. For example, the present technology can generate IL-1ra quicker and/or in greater quantities as compared to the methods described in U.S. Pat. No. 6,623,472, Reincke et al., issued Sep. 23, 2003; U.S. Pat. No. 6,713,246, Reinecke et al., issued Mar. 30, 2004; and U.S. Pat. No. 6,759,188, Reinecke et al., issued Jul. 6, 2004; and the methods described in U.S. Patent Application Publication No. 2010/0055087, Higgins et al., U.S. Patent Application Publication No. 2009/0220482, Higgins et al., and PCT Application Publication No. WO/2009/108890, Higgins et al.

Without limitation to the mechanism, utility, or function of the present technology, the solid extraction material appears to serve as an activator of IL-1ra production by the white blood cells. Likewise, electromagnetic stimulation of the white blood cells seems to increase the rate of IL-1ra production and/or the amount of IL-1ra produced as compared to white blood cells that are only contacted with the solid extraction material. In this manner, the contacting and stimulating aspects of the present methods appear to function in a synergistic fashion to generate a solution rich in IL-1ra.

As shown at step 130 of FIG. 1, the liquid comprising white blood cells 110 is contacted with a solid extraction material 120. The liquid comprising white blood cells 110 can be whole blood, bone marrow aspirate, adipose tissue, fractions thereof, and mixtures thereof. For example, platelet-rich plasma is a fraction of whole blood that can comprise white blood cells. Bone marrow aspirate also includes concentrated bone marrow aspirate, which can be prepared by removing liquid from bone marrow aspirate.

The liquid comprising white blood cells can also include a liquid comprising concentrated white blood cells which refers to a liquid having a concentration of white blood cells greater than found in whole blood. Concentrated white blood cells can be prepared by mixing a tissue or tissue fraction comprising white blood cells with a solid support, such as magnetic beads, coupled to an antibody operable to bind mononuclear leukocytes. For example, the tissue or tissue fraction comprising white blood cells can be whole blood, bone marrow aspirate, adipose tissue, fractions thereof, and mixtures thereof. Mononuclear leukocytes bound by the antibody are then collected (e.g., retained by a magnet) while liquid with unbound cells or other tissue components is removed and/or washed away. The bound or retained white blood cells provide the concentrated white blood cells.

Examples includes antibodies that can be coupled to a solid support, such as magnetic beads, where the antibody is directly coupled to the support or is coupled via one or more molecules such as a second antibody or other affinity couple. In some embodiments, a specific binding member (e.g., an antibody) that selectively binds white blood cells is used to collect the white blood cells from the sample by magnetic capture. Preferably, the specific binding member is either used to coat magnetic beads for direct capture, or is used in biotinylated form for indirect capture of white blood cells by streptavidin-coated magnetic beads.

The specific binding member that selectively binds white blood cells can be an antibody that binds white blood cells but does not appreciably bind other cells, such as red blood cells. Examples include antibodies to CD3, CD11b, CD14, CD17, CD31, CD45, CD50, CD53, CD63, CD69, CD81, CD84, CD102, or CD166. Antibodies can be tested for their ability to bind white blood cells using methods known in the art. For example, an antibody can be bound to a solid support, such as a bead, membrane, or column matrix, and following incubation of the liquid comprising white blood cells with the antibody, unbound components can be washed and removed from the solid support.

Concentrated white blood cells can also be prepared by passing a tissue or tissue fraction comprising white blood cells through a size exclusion filter. The filter can have a pore size that retains the white blood cells and allows liquid and components of the tissue or tissue fraction smaller than the white blood cells to pass through. Alternatively, the filter can have pore size that allows the white blood cells to pass through while retaining components of the tissue or tissue fraction larger than white blood cells. Examples of such filters and devices to concentrate white blood cells via filtration include various leukocyte reduction or depletion filters known in the art. Examples include the LeukoGuard™ and Leukotrap™ filters from Pall Life Sciences (Ann Arbor, Mich.), and include those described in U.S. Pat. No. 6,645,388, Sheikh-Ali et al., issued Nov. 11, 2003 and U.S. Pat. No. 5,895,575, Kraus et al., issued Apr. 20, 1999, which are incorporated herein by reference.

The solid extraction material 120 can include various materials that provide a particular surface area to contact the cells. The solid extraction material may comprise a continuous material or may be discontinuous and comprise a plurality of separate particles. For example, the solid extraction material may be in the form of a plurality of beads, fibers, powder, a porous material, or a surface of a container comprising the liquid containing the cells. The solid extraction material may comprise geometric forms having various cross-sectional shapes, such as spherical, oval, or polygonal, among others. The solid extraction material can also comprise a continuous porous network, similar to a sponge, or can include a plurality of individual porous particles. The solid extraction material may also provide a larger surface area by being porous in comparison to a non-porous material.

In some embodiments, the solid extraction material includes particles having a large aspect ratio, for example, where the particles are needle-like in shape. The solid extraction material may also be formed as long fibers and may be or take a form similar to glass wool.

In some cases, the solid extraction material can comprise the internal walls of a container holding the liquid comprising white blood cells. For example, the solid extraction material may comprise the lumen of a syringe that contains the liquid comprising white blood cells. Other containers include tubes, such as centrifuge tubes, or a blood fractionation device or concentrator assembly as described elsewhere herein.

Where the solid extraction material is a continuous material, such as a porous sponge-like material, the solid extraction material can be used in an amount sufficient to soak up or include substantially the entire liquid volume of white blood cells within the pores or interstices of the solid extraction material. Where the solid extraction material is a discontinuous material, such as a plurality of particles, the solid extraction material can be combined with the liquid containing the cells to form a slurry-like composition. The slurry can vary in consistency from paste-like, having a high-solids fraction, to a readily flowable slurry having a low-solids fraction.

The solid extraction material can provide a large surface area with which to contact the cells. However, in some cases, the solid extraction material can be further treated to increase its surface area, for example, by physically or chemically etching or eroding the surface of the solid extraction material. With respect to chemical etching, a corrosive agent can be used to modify the surface of the solid extraction material depending on the nature of the material. The modified surface may be produced by employing an alkali or an acid, for example chromosulphonic acid, in particular about 20% to about 80% in strength, preferably about 50% chromosulphonic acid. The solid extraction material can be incubated with the corrosive agent for about 5 min to about 30 min in order to chemically etch the surface and increase the surface area. The solid extraction material can then be washed to remove the corrosive agent. For example, the solid extraction material can include the internal walls of a container for holding the liquid comprising white blood cells where the internal walls are etched to subsequently increase the surface area in contact with the liquid.

Various polymers, metals, ceramics, and glasses can be used as the solid extraction material. These include, for example, a continuous solid extraction material of glass or a plurality of glass particles, glass wool, a continuous solid extraction material of metal such as titanium, a plurality of metal beads, metal powder, and combinations thereof. A continuous solid extraction material of metal can include a block or other three-dimensional shape formed of porous metal or metal alloys with an open cell structure. The solid extraction material may include various beads or particles of various sizes including substantially spherical beads. Beads include polystyrene beads, polyacrylamide beads, glass beads, metal (e.g., titanium) beads, or any other appropriate beads. Beads may be any size appropriate for the container and the amount of liquid comprising white blood cells being used. In some instances, bead sizes can range from about 0.001 millimeters to about 3 millimeters in diameter. Where the bead size is sufficiently small, the beads can appear more like a powder.

Surface contact with the solid extraction material can activate the cells and the solid extraction material can, in some cases, assist in the separation and concentration of the resulting solution rich in IL-1ra. For example, in the case of a porous solid extraction material, a portion of the liquid comprising the cells can enter the pores and remain therein. Cells in the liquid may contact this additional surface area. In some embodiments, the pores are too small for the cells to enter, but a portion of the liquid can enter the pores. Liquid can be removed from the solid extraction material and pores by centrifuging, for example. In some embodiments, the solid extraction material may comprise a hygroscopic material, such as desiccating polyacrylamide beads, that absorbs a portion of the liquid, thereby concentrating materials that are not absorbed into the hygroscopic material.

Various examples of suitable solid extraction material materials include glasses, minerals, polymers, metals, and polysaccharides. Minerals include corundum and quartz. Polymers include polystyrene, polyethylene, polyvinyl chloride, polypropylene, and polyacrylamide. Metals include titanium. Polysaccharides include dextran and agarose.

Sterilization of the solid extraction material can be performed using techniques known in the art in order to prevent contamination of the liquid comprising white blood cells. For example, heat and pressure sterilization methods, such as autoclaving, may be used depending on the particular composition of the solid extraction material. Alternative methods, such as chemical sterilization or irradiation, can be used where the solid extraction material may be adversely affected by the autoclaving process.

In some embodiments, the liquid comprising white blood cells and the solid extraction material are agitated to more thoroughly mix these components during contact. The agitation may be accomplished by inverting, shaking, rocking, stirring, or vortexing the liquid and solid extraction material. Agitation may increase contact of the cells within the liquid with the solid extraction material. Agitation may be performed once, repeated multiple times, repeated periodically, or may be continuous. The liquid comprising the cells and the solid extraction material may also be agitated while the liquid is stimulated with the electromagnetic field.

The liquid comprising white blood cells can be stimulated with an electromagnetic field, as indicated at 140 in FIG. 1. It should be noted that in some embodiments the stimulation of the liquid comprising the cells can be performed prior to contacting the liquid and the solid extraction material. That is, the order in which the contacting and stimulating steps of the present methods are initiated can be reversed. However, it is preferred that at least a portion of the contacting step and at least a portion of the stimulating step overlap in time such that the liquid comprising the cells is concurrently in contact with the solid extraction material and stimulated with the electromagnetic field.

Stimulating the liquid comprising white blood cells with an electromagnetic field may involve various forms of electromagnetic stimulation, such as a pulsed electromagnetic field or a capacitively coupled electromagnetic field. In some embodiments, the liquid is stimulated using a power source coupled to a stimulation coil. The current passing through the coil produces a pulsing magnetic field which induces in the liquid a pulsing electric field. The coil may partially surround the liquid as it is held within a container, such as a tube or syringe. The coil may be integrated into to the container holding the liquid comprising white blood cells or may be removable. For example, a plastic tube can be formed with an integrated coil or the coil can be temporarily coupled to the container or placed within the container; for example, the tube can be configured so that the coil can be snapped onto the container. The power source can be coupled to the coil as needed to perform the stimulating step.

Stimulation of the liquid with an electromagnetic field may also include placing at least two electrodes across the liquid. Electrical energy may then be applied to the electrodes so as to capacitively couple the electrodes and generate the electromagnetic field therebetween. The electromagnetic field is therefore able to pass through the liquid so as to increase the rate and/or amount of IL-1ra production. In other embodiments, electrodes can be used to produce a direct current or one or more coils can be used to produce a pulsed electromagnetic field.

The strength of the electromagnetic field during stimulation can be at least about 0.5 microvolts per centimeter, whether produced by direct current, capacitively coupled current, or pulsed electromagnetic field. In the case of a direct current electrode, the amplitude of the current can be from about 1 to about 200 microamperes, and in some embodiments, the amplitude may be from about 20 to about 100 microamperes. In still further embodiments, the current may be about 20, about 60, or about 100 microamperes. It should be understood, however, that the amplitude of the current may be of other suitable magnitudes.

The electromagnetic field applied during the stimulating step may be constant or vary over time. For example, a sinusoidal time varying electromagnetic field can be applied using the electrodes placed across the liquid. Such a sinusoidal time varying electromagnetic field can have a peak voltage across the electrodes from about 1 volt to about 10 volts, and in some embodiments, the peak voltage can be about 5 volts. The corresponding electric field produced can have an amplitude of from about 0.1 millivolt per centimeter (mV/cm) to about 100 mV/cm, and in some embodiments can be about 20 mV/cm. The sinusoidal time varying electric field may have a frequency of from about 1,000 Hz to about 200,000 Hz, and in some embodiments the frequency may be about 60,000 Hz.

The electromagnetic field applied to the liquid may also be a pulsed electromagnetic field. The pulsed electromagnetic field can be induced using an external coil and a pulse generator. In this regard, a pulsed electromagnetic field may have a pulse duration of from about 10 microseconds per pulse to about 2000 microseconds per pulse. The pulse duration in one embodiment can be about 225 microseconds. The pulses may include electromagnetic bursts, in which a burst can comprise from 1 pulse to about 200 pulses. Alternatively, the electromagnetic field may have bursts that comprise from about 10 pulses to about 30 pulses. In this regard, in one embodiment each burst may comprise about 20 pulses.

The frequency at which bursts in the pulsed electromagnetic are applied may vary. In this regard, bursts can be repeated at a frequency of from about 1 Hz to about 100 Hz in some embodiments, and can be repeated at a frequency of about 10 Hz to about 20 Hz in other embodiments. Furthermore, bursts can repeat at a frequency of about 1.5 Hz, about 15 Hz or about 76 Hz. A burst can have a duration from about 10 microseconds up to about 40,000 microseconds. In this regard, a burst can have a duration of about 4.5 milliseconds.

Suitable devices for generating a capacitively coupled electromagnetic field include SpinalPak® spinal stimulator (EBI, L. P., Parsippany, N.J.) or a DC stimulation device such as an SpF® XL IIb spinal fusion stimulator (EBI, L. P., Parsippany, N.J.). Pulsed electromagnetic fields can be produced using various known methods and apparatuses, such as using a single coil or a pair of Helmholtz coils. For example, a suitable apparatus includes the EBI Bone Healing System® Model 2001 (EBI, L. P., Parsippany, N.J.) and the BTBS stimulation coil. With respect to direct current, an electric field may be generated using any known device for generating a direct current electric field, such as for example, the Osteogen™ implantable bone growth stimulator (EBI, L. P., Parsippany, N.J.). Other suitable devices for generating electromagnetic fields may be used.

Electromagnetic stimulation of the liquid comprising white blood cells can be continued and/or repeated as desired with respect to contacting the liquid and the solid extraction material. It should be understood, however, that the step of stimulating the liquid with an electromagnetic field includes fields other than, or in addition to, electric or electromagnetic fields associated with ambient conditions (such the electromagnetic fields generated by casual exposure to radios, telephones, desktop computers or similar devices).

In some embodiments, both the contacting 130 and stimulating 140 steps as shown in FIG. 1 are performed in less than about 1 hour. The contacting and stimulating steps can also be performed at temperatures ranging from about 20° C. to about 37° C. In a preferred embodiment, the temperature of the liquid comprising white blood cells is kept at about 37° C. during the contacting and stimulating steps. One or both of the contacting and stimulating steps are typically performed ex vivo.

In some embodiments, the solution rich in IL-1ra 150, generated from the contacting 130 and stimulating 140 steps, as shown in FIG. 1, is separated from the solid extraction material. Separation from the solid extraction material can be performed in various ways. For example, the solution rich in IL-1ra may be removed from the solid extraction material using a syringe, by filtering the solution rich in IL-1ra, by centrifuging the solution rich in IL-1ra and the solid extraction material, or by using methods suitable for separating a liquid from a solid extraction material that are known in the art. Various separation techniques may be combined; for example, where the solution rich in IL-1ra is removed with a syringe, the residual solution contained within a porous solid extraction material can be subjected to centrifugation, and any solution that sediments may also be removed with the syringe. In some embodiments, the solution rich in IL-1ra can removed from the solid extraction material using pressure, for example when the solid extraction material is resilient and sponge-like, or can be drawn out using vacuum.

In some embodiments, the container in which the solution rich in IL-1ra is generated can be configured to aid in separating the solution from the solid extraction material. For example, the container may include a filter, mesh screen, or glass frit on one side, on the bottom, or on the container cap or lid. The container can then be centrifuged where the liquid passes through the filter, mesh, or frit and the solid extraction material and other materials, such as cells, are retained. In some cases, only the solid extraction material is retained and substantially all of the other materials pass through the filter, mesh, or frit. In this manner, the solution rich in interleukin-1 receptor antagonist can be centrifuged and collected into a fresh container, for example. Where the surface of a container forms the solid extraction material, the separating includes removing the liquid from the container.

Figure 2:
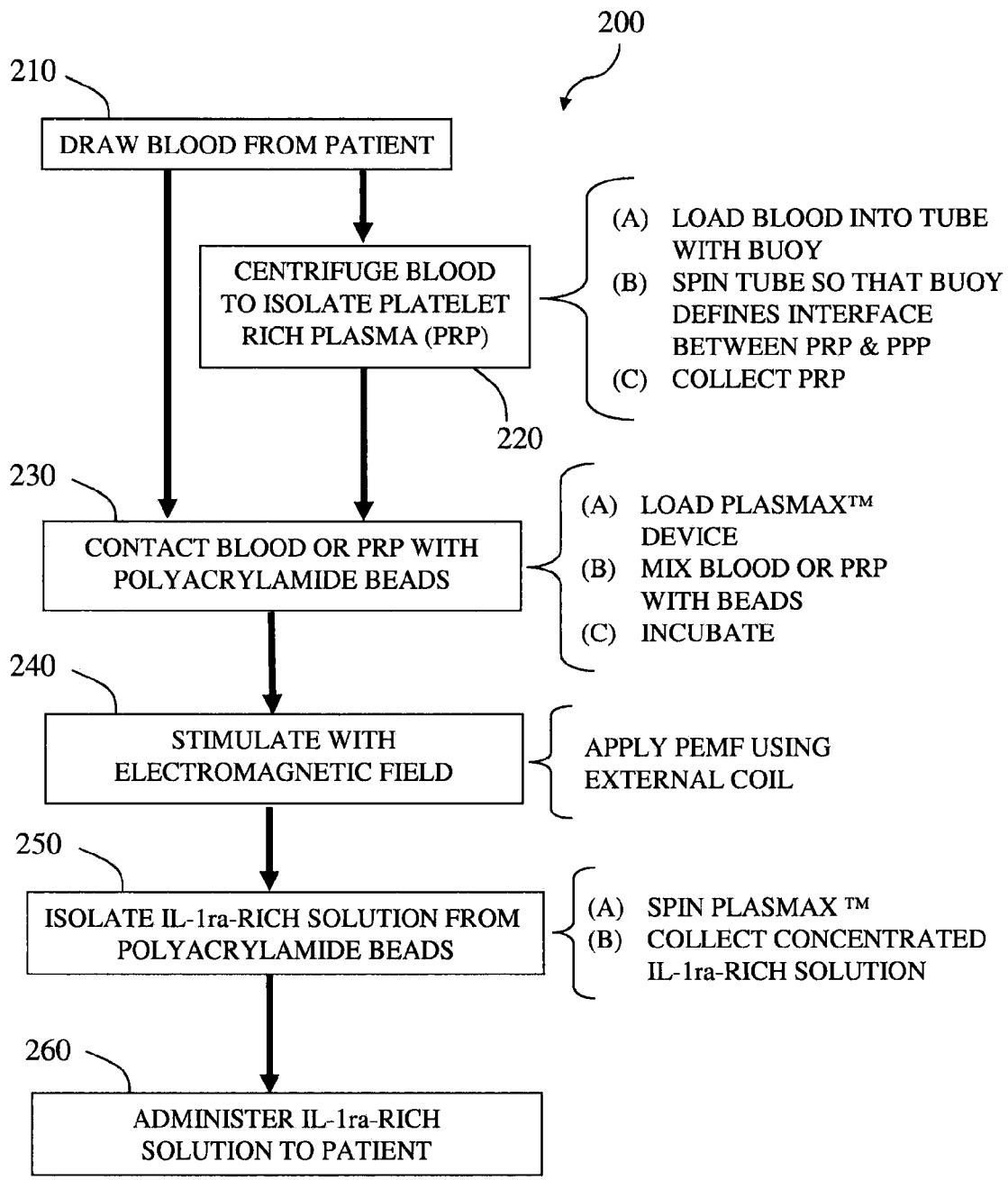
FIG. 2 is a diagrammatic illustration of another method to generate a solution rich in IL-1ra according to an embodiment of the present technology.

Referring now to FIG. 2, another method 200 for generating a solution rich in IL-1ra is shown. Blood is drawn from a patient, such as a human subject, at step 210. As further discussed below, this blood may be used directly in step 230, or may be processed to create a blood fraction in step 220. The blood or blood fraction provides a liquid comprising white blood cells. As used herein, platelet-rich plasma (PRP) is understood to include white blood cells and can be used as the liquid comprising white blood cells in the present methods and systems. For example, as shown in step 220, the blood can be centrifuged to isolate PRP that contains white blood cells and platelets. In some embodiments, the liquid comprising white blood cells includes the buffy coat layer formed following sedimentation of whole blood.

Figure 4:
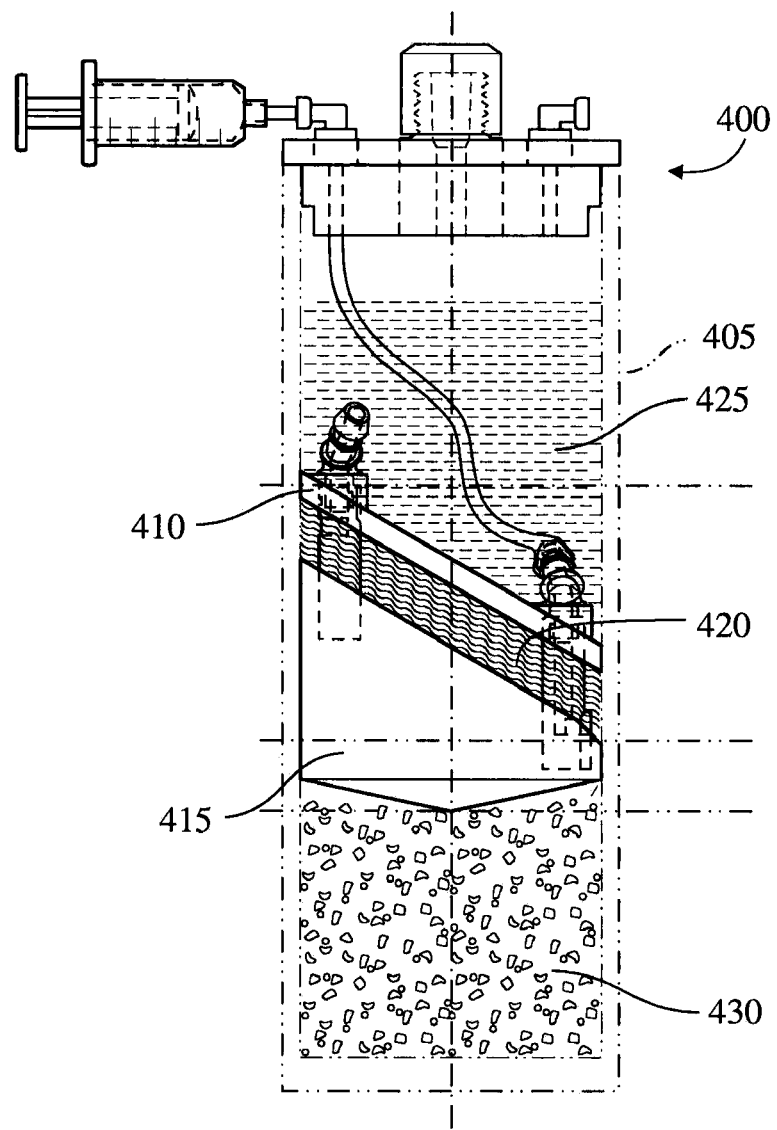
FIG. 4 is a partial cross-sectional view of a representative device used for isolating a liquid comprising white blood cells according to an embodiment of the present technology.

One example of a device that may be used for isolating platelet-rich plasma at step 220 is shown in FIG. 4. In this regard, the device 400 includes a container 405, such as a tube, that is placed in a centrifuge after being filled with blood. The container 405 includes a buoy system having an isolator 410 and a buoy 415. The buoy 415 has a selected density which is tuned to reach a selected equilibrium position upon centrifugation; this position lies between a more dense blood fraction and a less dense blood fraction. During centrifugation, the buoy 415 separates the blood within the container 405 into at least two fractions, without substantially commingling the fractions, by sedimenting to a position between the two fractions. In this regard, the isolator 410 and the buoy 415 define a layer comprising platelet-rich plasma 420, while less dense platelet-poor plasma 425 generally fractionates above the isolator 410, and more dense red blood cells 430 generally fractionate below the buoy 415.

Following centrifugation of the device 400, a syringe or tube may be interconnected with a portion of the buoy system to extract the platelet-rich plasma. In various embodiments, such devices may be used to generate platelet-rich plasma that includes a platelet concentration up to about 8-fold higher than whole blood and a white blood cell concentration up to about 5-fold higher than whole blood. The platelet rich plasma may comprise from about 80% to about 90% of the white blood cells present in the whole blood. Commercially available embodiments of such devices include the GPS® II Platelet Concentrate System, from Biomet Biologics, LLC (Warsaw, Ind., USA) and GPS® III Platelet Separation System, from Biomet Biologics, LLC (Warsaw, Ind., USA).

Devices that may be used to isolate platelet rich plasma at step 220 in FIG. 2 include those described, for example, in U.S. Pat. No. 6,398,972, Blasetti et al., issued Jun. 4, 2002; U.S. Pat. No. 6,649,072, Brandt et al., issued Nov. 18, 2003; U.S. Pat. No. 6,790,371, Dolocek, issued Sep. 14, 2004; U.S. Pat. No. 7,011,852, Sukavaneshvar et al., issued Mar. 14, 2006; U.S. Patent Application Publication No. 2004/0251217, Leach et al., published Dec. 16, 2004 (incorporated by reference herein); U.S. Patent Application Publication No. 2005/0109716, Leach et al., published May 26, 2005 (incorporated by reference herein); U.S. Patent Application Publication No. 2005/0196874, Dorian et al., published Sep. 8, 2005 (incorporated by reference herein); and U.S. Patent Application Publication No. 2006/0175242, Dorian et al., published Aug. 10, 2006 (incorporated by reference herein).

Other methods may be used to isolate platelet-rich plasma at step 220. For example, whole blood can be centrifuged without using a buoy system, whole blood may be centrifuged in multiple stages, continuous-flow centrifugation can be used, and filtration can also be used. In addition, a blood component including platelet-rich plasma and white blood cells can be produced by separating plasma from red blood cells using a slow speed centrifugation step to prevent pelleting of the platelets. In other embodiments, the buffy coat fraction formed from centrifuged blood can be separated from remaining plasma and resuspended to form platelet-rich plasma including white blood cells.

In addition to the GPS® Platelet Concentrate and Separation Systems, a variety of other commercially available devices may be used to isolate platelet-rich plasma at step

220, including the Magellan™ Autologous Platelet Separator System, commercially available from Medtronic, Inc. (Minneapolis, Minn., USA); SmartPReP™, commercially available from Harvest Technologies Corporation (Plymouth, Mass., USA); DePuy (Warsaw, Ind., USA); the AutoloGel™ Process, commercially available from Cytomedix, Inc. (Rockville, Md., USA); the GenesisCS System, commercially available from EmCyte Corporation (Fort Myers, Fla., USA); and the PCCS System, commercially available from Biomet 3i, Inc. (Palm Beach Gardens, Fla., USA).

Referring again to FIG. 2, the blood drawn from the subject at step 210 may be mixed with an anticoagulant prior to subsequent use in steps 220 or 230. Suitable anticoagulants include those known in the art, such as heparin, citrate phosphate dextrose (CPD), ethylenediaminetetraacetic acid (EDTA), acid citrate dextrose solution (ACD), and mixtures thereof. The anticoagulant may be placed in the syringe used for drawing blood from the subject, or may be mixed with the blood after it is drawn.

Alternatively, or in addition, blood from step 210 that is not subjected to centrifugation in step 220 can be combined with a solid extraction material comprising polyacrylamide beads in step 230 and incubated. This option is illustrated in FIG. 2 by the arrow running directly from step 210 to step 230. In this case, the polyacrylamide beads activate production of IL-1ra in the blood, but the concentration of IL-1ra may be lower compared to using platelet-rich plasma containing white blood cells or platelets or another liquid volume of white blood cells where the cells have been concentrated relative to whole blood.

A liquid comprising white blood cells may also be prepared using other methods known in the art. For example, white blood cells may be prepared from whole blood by lysing red blood cells or by centrifugation of whole blood utilizing a density gradient where the white blood cells sediment to the bottom of a centrifuge tube. An example of density centrifugation includes methods employing the Ficoll-Paque™ Plus products (GE Healthcare Bio-Sciences, Piscataway, N.J., USA). In some cases, a density gradient may be used to further separate mononuclear and polymorphonuclear cells. White blood cells may also be prepared from whole blood using filtration; an example includes the Acelere™ MNC Harvest System (Pall Life Sciences, Ann Arbor, Mich., USA). White blood cells can also be obtained from bone marrow.

As shown at step 230 of FIG. 2, the platelet-rich plasma from step 220 is contacted with a solid extraction material comprising polyacrylamide beads. In some embodiments, the platelet-rich plasma is incubated with desiccating polyacrylamide beads for a time effective to remove a portion of the liquid in the platelet-rich plasma. The incubation may be carried out over a period from about 30 seconds to about 72 hours and may be carried out at a temperature from about 20° C. to about 41° C. For example, the incubation may be from about one minute to about 48 hours, from about 5 minutes to about 12 hours, or from about 10 minutes to about 6 hours. In some embodiments, the incubation is conducted at about 37° C. In some embodiments the platelet-rich plasma is not incubated, but is contacted with the polyacrylamide beads for only so long as necessary to perform subsequent processing. The contacting may occur at ambient conditions, e.g., at a temperature of about 20-25° C.

Polyacrylamide beads used as the solid extraction material in step 230 can be formed by polymerizing acrylamide monomer using controlled and standardized protocols as known in the art to produce relatively uniform beads formed of polyacrylamide gel. In general, polyacrylamide is formed by polymerizing acrylamide with a suitable bifunctional crosslinking agent, most commonly N,N'-methylenebisacrylamide (bisacrylamide). Gel polymerization is usually initiated with ammonium persulfate and the reaction rate is accelerated by the addition of a catalyst, such as N,N,N',N'-tetramethylethylenediamine (TEMED). In various embodiments, polyacrylamide beads comprise 0.5 micromole of carboxyl groups per milliliter of beads, imparting a slight anionic character (negative charge). The beads are also typically resistant to changes in pH, and are stable in many aqueous and organic solutions. By adjusting the total acrylamide concentration, the polyacrylamide gel can be formed in a wide range of pore sizes. Moreover, the polyacrylamide beads can be formed in many sizes and can have relatively uniform size distributions. Bead size may range from several micrometers in diameter to several millimeters in diameter. For example, various types of Bio-Gel™ P polyacrylamide gel beads (Bio-Rad Laboratories, Hercules, Calif., USA) have particle sizes ranging from less than about 45 μm up to about 180 μm. Polyacrylamide beads are also available from SNF Floerger (Riceboro, Ga., USA), Pierce Biotechnology, Inc. (Rockford, Ill., USA), and Polymers, Inc. (Fayetteville, Ark., USA).

Once polymerized, polyacrylamide beads can be dried and stored in a powder-like form. The dry beads are insoluble in water but can swell considerably upon being rehydrated. Rehydration returns the polyacrylamide beads to a gel consistency that can be from about two to about three times the dry state size. Thus, dry polyacrylamide beads (i.e., desiccating polyacrylamide beads) may be used to absorb a portion of a liquid volume, including solutes smaller than the bead pore size, and can serve to concentrate the IL-1ra produced by the white blood cells. For example, combining dry polyacrylamide beads with the blood and/or platelet-rich plasma in step 230 activates production of IL-1ra by the white blood cells and also reduces the total liquid volume as the dry beads rehydrate and swell.

Without limiting the mechanism, utility or function of the present technology, the polyacrylamide beads may serve as an activator of IL-1ra production by the white blood cells. Therefore, in the case of dry polyacrylamide beads, not only is liquid being absorbed from the volume of white blood cells, thereby concentrating the IL-1ra formed, but the beads further serve as a surface to stimulate IL-1ra production by the white blood cells. For example, IL-1ra collected using platelet-rich plasma obtained using a device according to FIG. 4, such as the GPS® II system, may yield about a 5-fold increase in IL-1ra concentration versus whole blood. The concentration of IL-1ra may then be increased about 40-fold or more, to a final concentration increase of about 200-fold, upon incubation and isolation of the IL-1ra-rich solution using a device according to FIGS. 5A and 5B, such as a Plasmax™ device (Biomet Biologics, LLC, Warsaw, Ind., USA), as described further below. Thus, the increase in the amount of IL-1ra likely not due to simply an increase in concentration by reducing the volume of the sample, but appears to be due in part to activation of the white blood cells and other growth factors from platelets by the polyacrylamide beads to increase production and/or release of IL-1ra.

With reference to FIG. 2, the platelet-rich plasma is stimulated with an electromagnetic field as shown at 240. A pulsed electromagnetic field (PEMF) is applied using a coil that is placed near the platelet-rich plasma. For example, one or more coils can be placed into or about a portion the container holding the platelet-rich plasma and polyacrylamide beads, such as the Plasmax™ device. In some cases, two coils are used where the container including the platelet-rich plasma is disposed between the coils. The PEMF can be applied using parameters described in U.S. Pat. No. 7,744,869 (issued Jun. 29, 2010), U.S. Pat. No. 7,520,849 (issued Apr. 21, 2009), and U.S. Pat. No. 6,955,642 (issued Oct. 18, 2005) all to Simon, which are incorporated herein by reference.

Following contact of the platelet-rich plasma with the polyacrymide beads and electromagnetic field stimulation, an IL-1ra-rich solution is generated and can be isolated from the beads, as indicated at step 250 in FIG. 2. Isolation of the solution rich in IL-1ra may be accomplished by drawing off the liquid volume and leaving the beads. In some cases, the beads may be sedimented by centrifugation prior to drawing off the IL-1ra-rich solution. Isolation may also be performed by filtration, where the polyacrylamide beads are retained by a filter and the IL-1ra-rich solution passes through the filter using centrifugal force or by using vacuum, for example. If the contacting with polyacrylamide beads at step 230 utilizes dry polyacrylamide beads, the liquid volume may be reduced as the beads swell upon rehydration, thereby concentrating the resulting IL-1ra-rich solution. To maintain the increased concentration, care should be taken in the isolation step 250 so as to avoid compressing the beads or drawing liquid out from the swollen beads. For example, high centrifugal force or high vacuum may collapse the beads and/or draw liquid out of the internal volume of the beads.

In some cases, contact of the platelet-rich plasma with polyacrylamide beads (as per step 230), electromagnetic field stimulation (as per 240), and the isolation of the resulting IL-1ra-rich solution (as per step 250), may be performed using a single device. An example of a device for incubating platelet-rich plasma with polyacrylamide beads is shown in FIGS. 5A and 5B. In this regard, the device 500 has an upper chamber 505 and a lower chamber 510. The upper chamber 505 has an end wall 515 through which the agitator stem 520 of a gel bead agitator 525 extends. The device 500 also has an inlet port 530 that extends through the end wall 515 and into the upper chamber 505. The device 500 also includes an outlet port 535 that communicates with a plasma concentrate conduit 540. The floor of upper chamber 505 includes a filter 545, the upper surface of which supports desiccated concentrating polyacrylamide beads 550.

During use, a fluid 555 containing white blood cells (e.g., platelet-rich plasma) is injected to the upper chamber 505 via the inlet port 530 and mixed with the polyacrylamide beads 550. The fluid 555 and polyacrylamide beads 550 may be mixed by rotating the agitator stem 520 and the gel bead agitator 525, to help mix the fluid 555 and beads 550. The mixed fluid 555 and polyacrylamide beads 550 are then incubated for the desired time at the desired temperature. During this time, the mixed fluid 555 and polyacrylamide beads 550 are stimulated with an electromagnetic field, such as a pulsed electromagnetic field applied using two coils placed across the portion of the upper chamber 505 including the mixed fluid 555 and polyacrylamide beads 550. The device 500 is then centrifuged so that liquid passes to the lower chamber 510 while the polyacrylamide beads 550 are retained by a filter 545, thereby separating the polyacrylamide beads 550 from the resulting solution 560 of IL-1ra that collects in the lower chamber 510. The solution 560 may be removed from the device via outlet port 535.

Exemplary devices of FIG. 5 are disclosed in U.S. Patent Application Publication No. 2006/0175268, Dorian et al., published Aug. 10, 2006; and U.S. Patent Application Publication No. 2006/0243676, Swift et al., published Nov. 2, 2006; both of which are incorporated by reference herein.

Such a device is commercially available as Plasmax™ Plus Plasma Concentrator, from Biomet Biologics, LLC (Warsaw, Ind., USA).

Referring again to FIG. 2, in step 260 the IL-1ra-rich solution is administered to a patient, such as a human or animal subject. The patient receiving the IL-1ra-rich solution may be the same patient from which the blood in step 210 is obtained or derived. In this case, the method provides an autologous preparation of IL-1ra. Administration may be performed using various means, such as by injection of the IL-1ra-rich solution using a syringe, surgical application, or application concomitant with another surgical procedure. It should be understood, however, that step 260 may comprise any biomedically acceptable process or procedure by which the IL-1ra-rich solution is implanted, injected, or otherwise administered at or in proximity to a site in order to mediate effects related to stimulation of the interleukin-1 receptor, such as inflammation. For example, for treating inflammation caused by arthritis, an autologous IL-1ra-rich solution may be administered to the patient via injection. Injection may be located at or into the synovial space of an inflamed joint, or otherwise at or near the joint.

Figure 3:
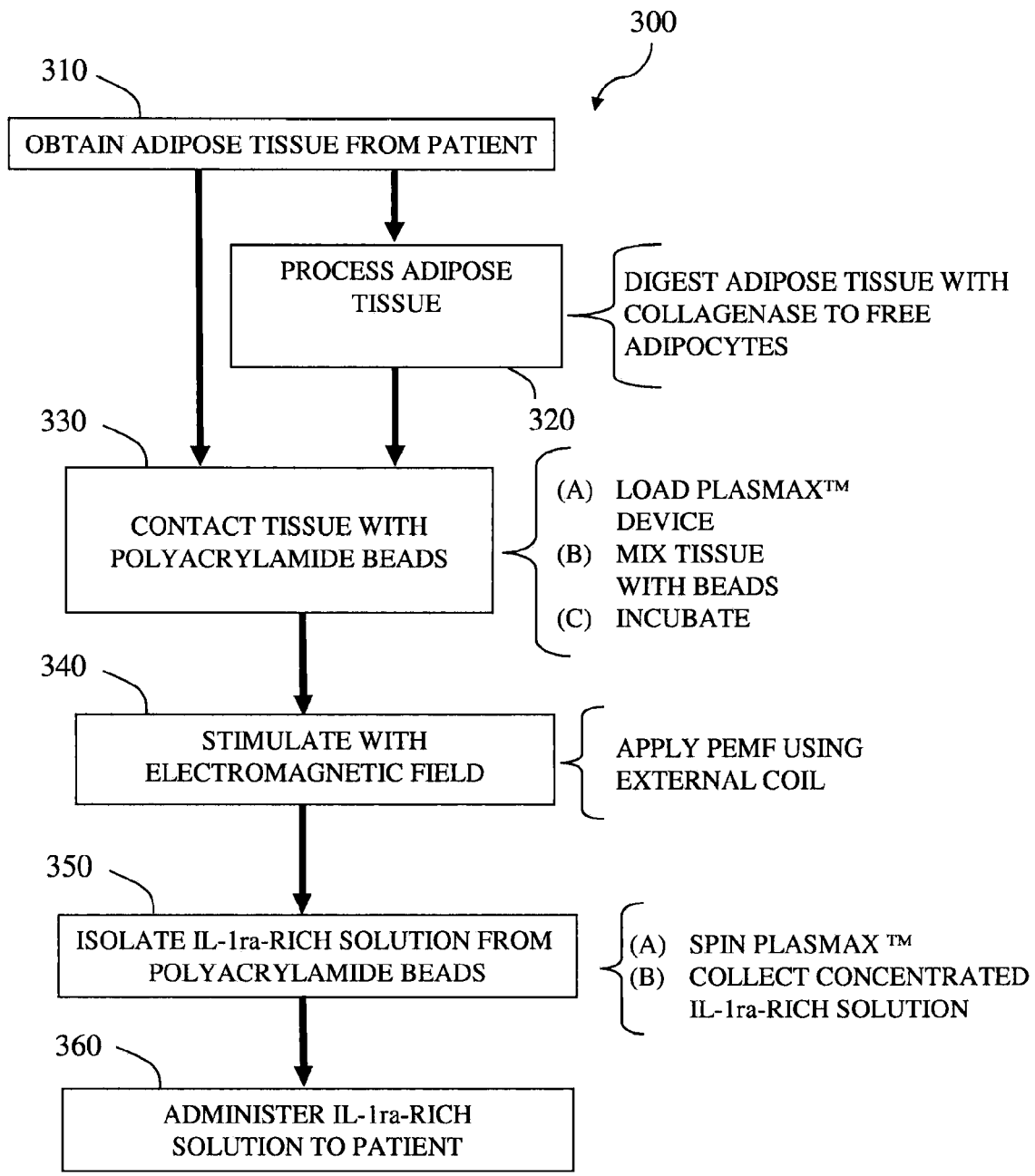
FIG. 3 is a diagrammatic illustration of another method to generate a solution rich in IL-1ra according to an embodiment of the present technology.

In a similar fashion to the method shown in FIG. 2, adipose tissue can be used to provide a liquid comprising adipocytes for use in another method 300 as diagrammatically shown in FIG. 3. In this case, adipose tissue is obtained from a patient in step 310 where the adipose tissue is further processed 320 or used directly as a liquid comprising adipocytes. The adipose tissue can be contacted and incubated 330 with a solid extraction material comprising polyacrylamide beads, stimulated with an electromagnetic field 340, and the IL-1ra-rich solution isolated 350 and administered 360 to the patient in the ways described for the analogous steps shown in FIG. 2. However, obtaining adipose tissue 310 and processing adipose tissue 320 can further include the following aspects.

The liquid volume of adipocytes can be part of isolated adipose tissue; where, for example, the adipose tissue may include other cell types. Contacting 330 of adipocytes and polyacrylamide beads may include incubating the liquid volume of adipocytes with the polyacrylamide beads for times ranging from about 30 seconds to about 24 hours, preferably less than about 1 hour, including the electromagnetic field stimulation 340. The contacting 330 may also include contacting a liquid volume comprising white blood cells with the polyacrylamide beads in addition to contacting the liquid volume of adipocytes with the polyacrylamide beads. The liquid volume of white blood cells can be whole blood, platelet rich plasma, or whole blood and platelet rich plasma. White blood cells can also be obtained from bone marrow.

Adipose tissue refers to any fat tissue, either white or brown adipose tissue, which may be derived from subcutaneous, omental/visceral, mammary, gonadal, or other adipose tissue sites. In some embodiments, adipose tissue is derived from human subcutaneous fat isolated by suction assisted lipectomy or liposuction. Adipocytes and other cells, which may include white blood cells, can be isolated and/or disaggregated from the adipose tissue and/or tissue portions using any suitable method, including methods known in the art, such as mechanical and breakdown centrifugation. Adipocytes and other cells also can be isolated using enzymatic digestion. For example, adipocytes and other cells can be isolated from lipoaspirate, treated by sonication and/or enzymatic digestion, and enriched by centrifugation. Adipocytes and other cells isolated from adipose tissue may be washed and pelleted one or more times.

Methods for isolating adipose tissue and adipocytes can include the following aspects. About 50 cc of adipose tissue can be collected by suction-assisted tumescent liposuction inside a specialized collection container attached to suction hoses and to a liposuction cannula. The collection container can have a gauze-type grid filter that allows the tumescent fluid to pass through and retains the solid adipose tissue. After collecting the adipose tissue, the collection container is removed from the suction device and reattached to a centrifugation device. The filter unit may further contain a filter having approximately a 100 micrometer pore size. Once the collection container containing the adipose tissue is attached to the centrifugation device, the tissue is sonicated. After sonication, the entire apparatus is inserted into a centrifuge bucket and centrifuged at about 300×g for about 5 minutes. After centrifugation, the collection container together with the filter unit is detached. The pellet containing the adipocytes and other cells can be resuspended in a biocompatible solution, such as autologous plasma, plasma concentrate, and/or platelet rich plasma.

Adipose tissue may also be treated with digestive enzymes and with chelating agents that weaken the connections between neighboring cells, making it possible to disperse the tissue into a suspension of individual cells, including adipocytes, without appreciable cell breakage. Following disaggregation, the adipocytes and other cells may be isolated from the suspension of cells and disaggregated tissue.

Various methods and devices for isolating and/or fractionating adipose tissue include those as described by U.S. Pat. No. 7,374,678 (issued May 20, 2008) and U.S. Pat. No. 7,179,391 (issued Feb. 20, 2007) to Leach et al. and U.S. Patent Application Publication Nos. 2009/0014391 (published Jan. 15, 2009), 2008/0283474 (published Nov. 20, 2008), and 2007/0208321 (published Sep. 6, 2007) to Leach et al. A device, such as the GPS™ Platelet Concentrate System (Biomet, Warsaw, Ind.), may be used to isolate adipocytes. These methods can include obtaining adipocytes and other cells by performing lipoaspiration on the patient to obtain adipose tissue, enzymatically digesting the adipose tissue, and separating and/or washing the adipocytes using these devices.

In some embodiments, isolation of adipose tissue can be performed by extraction of tissue by standard lipoaspiration, isolation from excised adipose tissue, or by using the VASER® ultrasound disruptor in combination with the VENTX™ cannula, available from Sound Surgical Technologies, LLC, Louisville, Colo.

Contact of the adipocytes and other cells, including white blood cells, with the surface of the solid extraction material (e.g., polyacrylamide beads) appears to stimulate IL-1ra production and secretion. There also appears to be a correlation between the amount of IL-1ra produced and the concentration of white blood cells, where the adipose tissue can include white blood cells. Thus, the present methods can use adipose tissue and disaggregated adipose tissue to obtain adipocytes, where white blood cells can be present in both the adipose tissue and the adipocytes obtained from adipose tissue.

Figure 6:
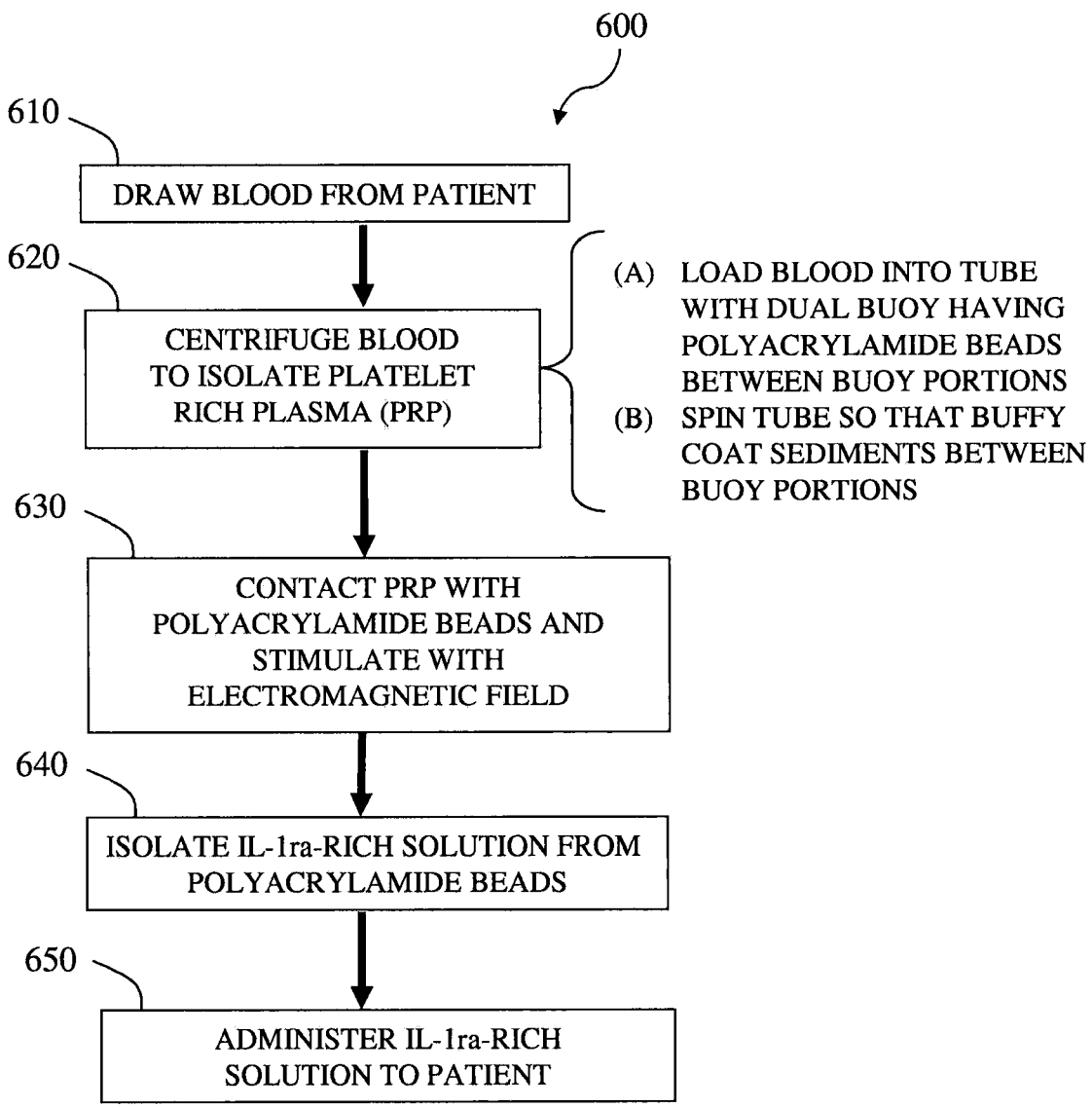
FIG. 6 is a diagrammatic illustration of another method to generate a solution rich in IL-1ra according to an embodiment of the present technology.

Referring to FIG. 6, another method 600 for generating a solution rich in IL-1ra is shown. In this case, blood is first drawn from a patient in step 610. Proceeding to step 620, the blood is centrifuged, to isolate platelet-rich plasma. As with the method of FIG. 2, the platelet-rich plasma may be isolated with various devices, such as the one shown in FIG. 4. For example, the device including a dual buoy mechanism can include polyacrylamide beads between the buoy 415 and isolator 410. The polyacrylamide beads may be dry or hydrated, as described in reference to step 230 for FIG. 2.

During centrifugation in step 620, platelet-rich plasma collects between the buoy 415 and isolator 410 and comes in contact with the polyacrylamide beads. The less dense platelet-poor plasma component forms above the platelet-rich plasma and the denser red blood cell component forms below. Once centrifugation is completed, the tube containing the separated blood components may be incubated for the desired time and at the desired temperature, indicated at step 630, where the platelet-rich plasma is further stimulated with an electromagnetic field. In this manner, IL-1ra is generated by the white blood cells within the mixture of platelet-rich plasma and polyacrylamide beads located between the buoy and isolator.

In cases where dry polyacrylamide beads are used, once centrifugation is complete in step 620, the upper platelet-poor plasma component and the lower red blood cell component may be removed from the tube prior to incubation, leaving the platelet-rich plasma and polyacrylamide bead mixture between the two buoy portions. Alternatively, the mixture of platelet-rich plasma and polyacrylamide beads may be removed from the tube. In either case, separation of the platelet-rich plasma and polyacrylamide bead mixture from fluid contact with the platelet-poor plasma and the red blood cell component allows subsequent swelling and rehydrating of dry polyacrylamide beads to effectively reduce the liquid volume of the platelet-rich plasma, further concentrating the resulting IL-1ra solution.

As shown at step 640, the IL-1ra-rich solution is isolated from the polyacrylamide beads following the contacting and stimulating in step 630. Separation of the IL-1ra-rich solution from the beads may be accomplished using various means, such as those described in reference to step 250 in FIG. 2. As shown at step 650, the IL-1ra-rich solution is then administered to a patient. Administration may be performed using various means, such as those described in reference to step 260 in FIG. 2.

Figure 7:
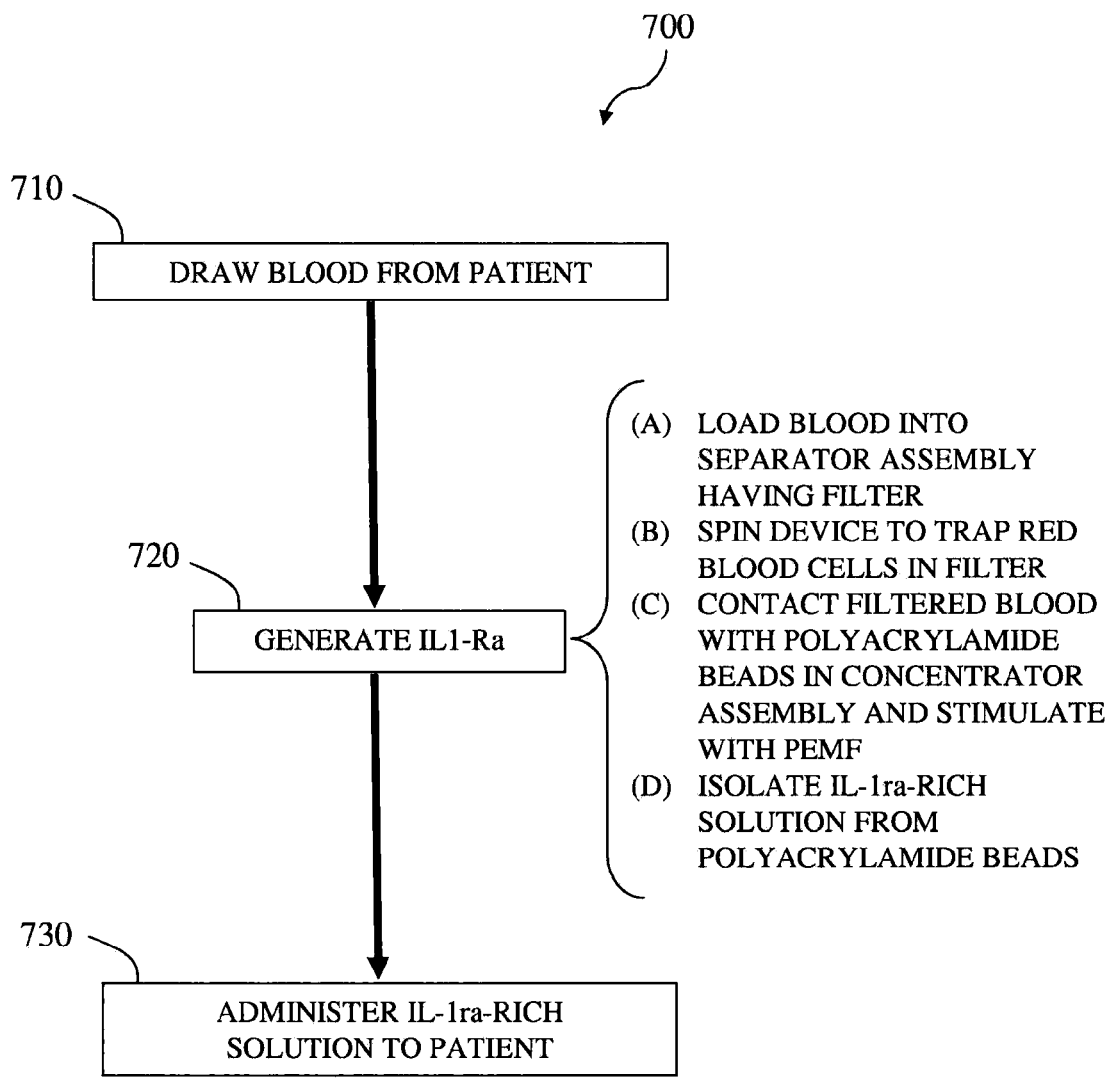
FIG. 7 is a diagrammatic illustration of another method to generate a solution rich in IL-1ra according to an embodiment of the present technology.

Referring now to FIG. 7, another method 700 for generating a solution rich in IL-1ra is shown. Blood is drawn from the patient in step 710. A large volume concentration device is used to filter the blood and effectively remove some of the blood components, as shown at step 720, in order to produce platelet-rich plasma containing white blood cells and platelets.

A suitable device for use in step 720 includes a separator assembly and a concentrator assembly. The separator assembly captures red blood cells in a filter, such as a felt filter. The filter has pores and passageways that are sized to receive and entrap red blood cells during centrifugation. The device captures the red blood cells by rotating blood at speeds in a balanced cylindrical separation chamber that is lined with the filter, where the separation chamber and filter are segmented by radially extending plates into separation zones. The rotational speed of the separation chamber allows separation of platelet-rich plasma, including white blood cells, in the separation zones.

The concentrator assembly can concentrate the platelet-rich plasma by absorbing liquid in the platelet-rich plasma using dry polyacrylamide beads, as described in reference to step 230 in FIG. 2. The platelet-rich plasma is contacted in a rotating concentrating chamber with the polyacrylamide beads to produce a platelet-rich plasma concentrate while the beads are stirred. The platelet-rich plasma and polyacrylamide bead mixture can then be stimulated with an electromagnetic field in the concentrator assembly to allow for the generation of IL-1ra, including any additional concentration of the solution due to swelling and absorption of liquid by the beads. The resulting IL-1ra-rich solution is collected by rotating the concentration chamber at a speed to separate platelet-rich plasma concentrate from the beads.

Examples of such devices include the Vortech™ Concentration System (Biomet Biologics, LLC, Warsaw, Ind., USA), and include those disclosed in U.S. Patent Application Publication No. 2006/0175244, Dorian et al., published Aug. 10, 2006 and U.S. Patent Application Publication No. 2006/0175242, Dorian et al., published Aug. 10, 2006, which are hereby incorporated by reference. These devices may be used in lieu of or in addition to using the tube having a buoy described in reference to step 220 in FIG. 2 to prepare platelet-rich plasma including white blood cells and platelets.

As shown at step 730, the IL-1ra-rich solution is then administered to a patient. Administration may be performed using various means, such as those described in reference to step 260 in FIG. 2.

Figure 8:
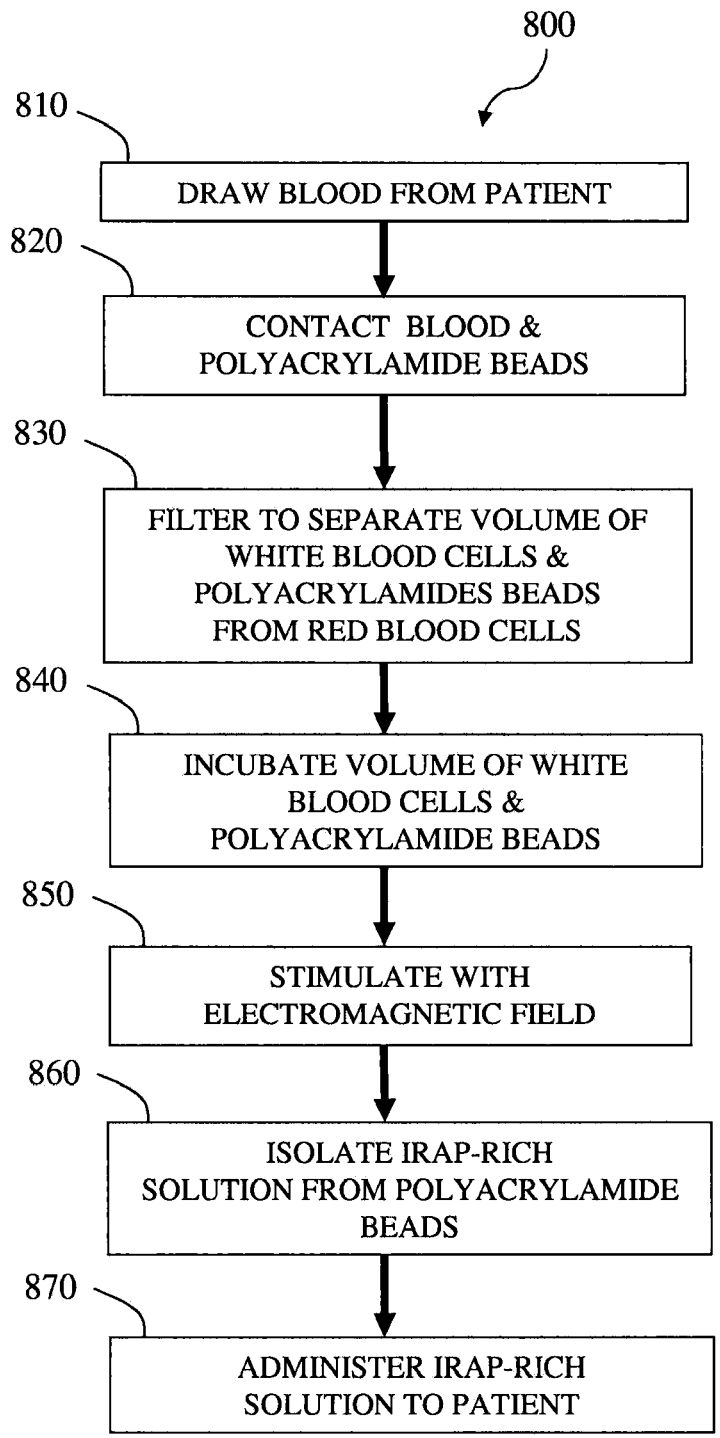
FIG. 8 is a diagrammatic illustration of another method to generate a solution rich in IL-1ra according to an embodiment of the present technology.

Referring to FIG. 8, another method 800 for generating a solution rich in IL-1ra is shown. Blood is drawn from the patient, as shown at step 810, and combined with polyacrylamide beads, as shown at step 820. The polyacrylamide beads may be dry or hydrated, as described in reference to step 230 in FIG. 2. Filtration is then used in step 830 to separate a volume of white blood cells and the polyacrylamide beads from red blood cells. Filtration may be accomplished using a single filter or a series of size exclusion filters to capture the white blood cells and the beads, while other blood components, such as red blood cells, pass with one or more filtrates. Once the filtration is complete, the volume of white blood cells and polyacrylamide beads is incubated, as shown at step 840, in order to activate the production of IL-1ra and further reduce the liquid volume, if dry polyacrylamide beads are used. At this point, the liquid volume of white blood cells is also subjected to an electromagnetic field to generate IL-1ra while the liquid is in contact with the polyacrylamide beads, as shown at step 850. Platelets may also be added to the liquid during the incubation in steps 840 and 850.

The IL-1ra-rich solution is isolated from the polyacrylamide beads in step 860. Various means of isolation may be used, such as by drawing off the liquid volume and leaving the beads. In some cases, the beads are sedimented by centrifugation prior to drawing off the IL-1ra-rich solution. Isolation may also be performed by filtration, where the polyacrylamide beads are retained by a filter and the IL-1ra-rich solution passes through the filter using force generated by a centrifuge or by using vacuum, for example. In some cases, the IL-1ra-rich solution is isolated from the polyacrylamide beads by drawing the solution through the same filter or series of filters used in step 830. The IL-1ra-rich solution may be drawn into a fresh collection chamber, or into a previously used filtrate collection chamber where the one or more earlier filtrates have been removed. The IL-1ra-rich solution is then administered to the patient, as shown at step 870.

The various preparations of IL-1ra-rich solutions produced by the present methods and systems may be sterilized by including a sterile filter to process the final isolated IL-1ra product. Similarly, an antibiotic may be included in the polyacrylamide beads during incubation or added at one or more of the various steps in the methods described herein.

The present technology provides improved methods for preparing solutions rich in IL-1ra, including autologous IL-1ra-rich solutions that reduce and/or substantially eliminate immunological issues that may arise when using non-autologous material or recombinant material. In addition, since the IL-1ra is produced by the patient's cells, natural post-translational modifications, such as glycosylation, are already present. This is not the case with most recombinant proteins since they are produced in prokaryotic hosts.

The solutions rich in IL-1ra produced with the present methods and systems can be characterized as comprising viable whole blood cells, and having increased concentrations of IL-1ra, soluble tumor necrosis factor receptors, including sTNF-rI and sTNFr-II, plasma proteins, and growth factors relative to whole blood. It is understood, however, the concentrations present in any given solution may vary depending on the initial levels of components present in the whole blood or plasma used in the present methods, and that increases in concentration are relative to those initial levels.

In general, IL-1ra can be present in the IL-1ra-rich solution at a concentration of at least about 10,000 pg/mL, at least about 25,000 pg/mL, or at least about 30,000 pg/mL. Plasma protein levels are typically present at concentrations of at least about 50 mg/mL, at least about 80 mg/mL, at least about 100 mg/mL, at least about 200 mg/mL, or at least about 250 mg/mL. In particular, albumin is present at a concentration of about 40 mg/mL, or at least about 100 mg/mL; and fibrinogen is present at a concentration of at least about 2 mg/mL or at least about 4 mg/mL. sTNF-r1 is typically present at concentrations greater than whole blood, such as at least about 1500 pg/mL. Increased concentrations of growth factors include: platelet-derived growth factor PGDF-AB, at concentrations of greater than 50,000 pg/mL, or greater than 70,000 pg/mL; transforming growth factor TGF-β1, at concentrations greater than 150,000 pg/mL, or greater than 190,000 pg/mL; insulin-like growth factor IGF-1, at concentrations greater than about 140,000 pg/mL, or greater than 160,000 pg/mL; basic fibroblast growth factor bFGF, at concentrations greater than 150,000 pg/mL, or greater than 170,000 pg/mL; and vascular endothelial growth factor VEGF, at concentrations greater than 1,200 pg/mL, or greater than 1,400 pg/mL. Concentrations of inflammatory cytokines (e.g., interleukin 1α, interleukin 1β, tumor necrosis factor-α and interleukin 10) are generally not significantly greater than whole blood, and may be lower. An example of specific levels of components is set forth in Table 1, below.

TABLE 1

Example of Composition Components

| Component | Concentration |
|---|---|
| plasma proteins-total | 286 mg/mL |
| albumin | 109 mg/mL |
| fibrinogen | 4.9 mg/mL |
| IL-1ra | 34,000-108,000 pg/mL |
|  | (whole blood = 200-800 pg/mL) |
| sTNF-RI | 270-3,450 pg/mL |
|  | (whole blood = 960 pg/mL) |
| IL-1 | below detection limit |
| IL-1 | 22 pg/mL |
|  | (whole blood = below detection limit) |
| TNF- | below detection limit |
| IL-10 | 1.6-9.06 pg/mL |
|  | (whole blood = 4.53 pg/mL) |
| Growth factors |  |
| PDGF-AB | 73,201 pg/mL |
| TGF-1 | 194,076 pg/mL |
| IGF-1 | 160,000 pg/mL |
| bFGF | 176 pg/mL |
| VEGF | 1,464 pg/mL |

The IL-1ra-rich solutions may be administered to mediate effects of IL-1 and attenuate signaling via the interleukin-1 receptor. The IL-1ra-rich solution may be used to block the biologic activity of naturally occurring IL-1, including inflammation and cartilage degradation associated with arthritis, by competitively inhibiting the binding of IL-1 to the interleukin-1 type receptor, which is expressed in many tissues and organs. For example, bone resorption and tissue damage such as cartilage degradation as a result of loss of proteoglycans due to IL-1 may be treated by administration of the IL-1ra-rich solution. In patients with arthritis, endogenous IL-1ra may not be found in effective concentrations in synovium and synovial fluid to counteract IL-1 concentrations in these patients, and hence the present IL-1ra-rich solution may be administered to treat these conditions and these sites. Dosing, administration, and frequency of treatment may be modified based on established medical practices to achieve effective treatment.

The present technology further provides methods for delivering IL-1ra. Such delivery methods can include a solution of IL-1ra and fibrinogen where the fibrinogen is activated to form a fibrin matrix that protects and retains the IL-1ra at a treatment site. The fibrin matrix can be formed in situ upon delivery of the IL-1ra.

Fibrinogen can be cross-linked into a three-dimensional matrix by activation with a clotting agent and calcium. Suitable clotting agents include thrombin (e.g., bovine, recombinant human, pooled human, or autologous), autologous clotting protein, and polyethylene glycol. Calcium may be in the form of a calcium salt, such as calcium chloride.

Figure 9A:
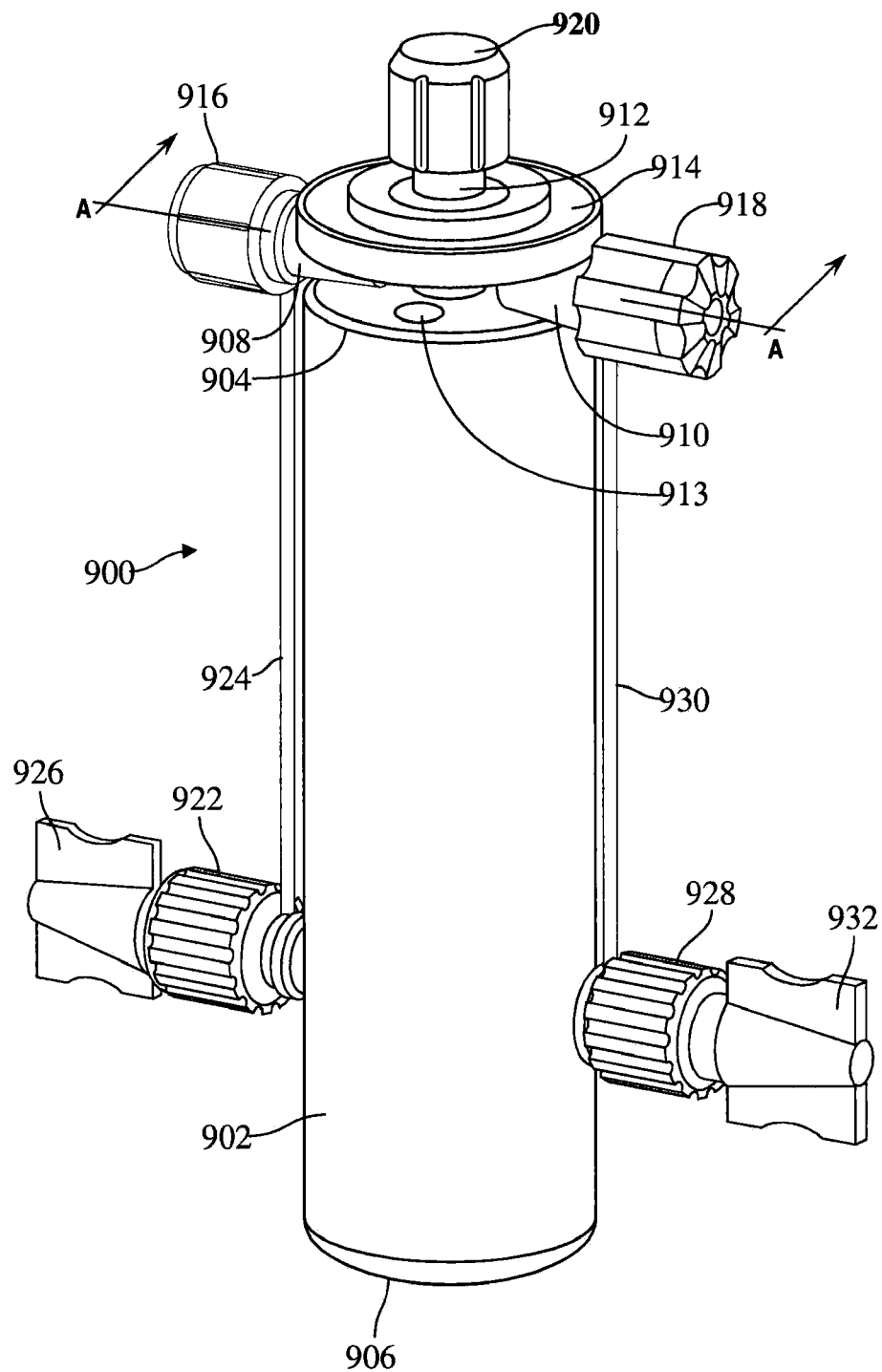
FIGS. 9A and 9B are an isometric view and a partial cross-sectional view, respectively, of a blood component isolation device which may be used in methods of the present technology.
Figure 9B:
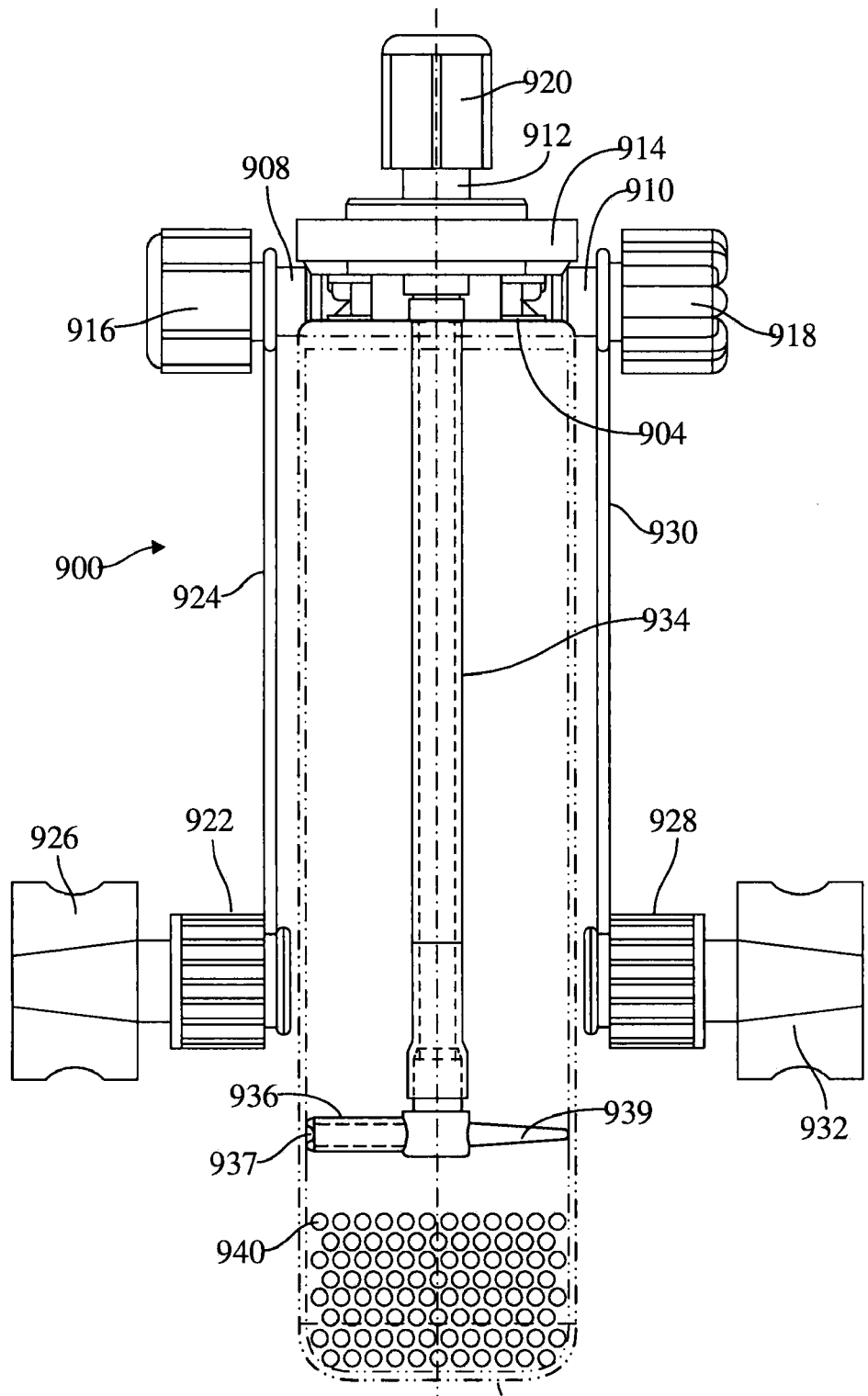

In some embodiments, the clotting agent comprises an autologous clotting protein, as a clotting fraction derived from a blood obtained from the patient to be treated. A suitable clotting fraction can be obtained by a process of: loading whole blood or plasma with a calcium solution (e.g., calcium chloride in ethanol) into a blood isolation device; heating the whole blood or plasma for at least about 20 minutes, at a temperature of at least about 20° C.; and isolating the clotting fraction. The isolating may be performed by centrifuging the heated whole blood or plasma. A suitable isolation device is depicted in FIGS. 9A and 9B. Such a device is commercially available as the Clotalyst™ Autologous Thrombin Collection System, sold by Biomet Biologics LLC, Warsaw, Ind., USA.

With reference to FIGS. 9A and 9B, the blood separation device 900 generally includes a body having a cylindrical wall along with a first end 904 and a second end 906 that define a main chamber 902. At the first end 904 is a first port 908, a second port 910, a third port 912, a vent 913, and a filter 914. Each of the first port 908, the second port 910, the third port 912, and the vent 913 extend through the first end 904 and permit fluid communication between an exterior of the device 900 and the main chamber 902. The first port 908 can be covered with a first cap 916, the second port 910 can be covered with a second cap 918, and the third port 912 can be covered with a third cap 920. A first replacement cap 922 for the first port 908 can be attached to the first port 908 with a first tether 924. A first cover 926 can be secured to the first replacement cap 922 when the first replacement cap 922 is not in use. A second replacement cap 928 for the second port 910 can be attached to the second port 910 with a second tether 930. A second cover 932 can be secured to the second replacement cap 928 when the second replacement cap 928 is not in use.

The first port 908 and the second port 910 each include a stop valve to prevent materials, such as glass beads 940, from exiting the main chamber 902 through the first and the second ports 908 and 910. The valves can be any suitable valve, such as a duck-billed valve.

With particular reference to FIG. 9B, the third port 912 includes an elongated tube portion 934 that extends within the main chamber 902. The elongated portion 934 extends from the first end 904 to a depth within the main chamber 902 to permit withdrawal of select materials, such as thrombin and other blood clotting factors, from within the main chamber 902. For example and as further described below, where the main chamber 902 includes whole blood, reagents (e.g., a calcium solution comprising calcium compound dissolved in ethanol or other suitable solvent), anticoagulant, and glass beads, incubation and centrifugation of this mixture forms a clotted mass of about including red blood cells, blood plasma, and glass beads at the second end 906 of the main chamber 902. On top of the clotted mass, at the side of the clotted mass nearest the first end 904, an effluent is formed comprising thrombin and various other clotting factors. The clotted mass at the second end 906 can be visually distinguished from the effluent. In order to extract thrombin and the other clotting factors using the elongated tube portion 934, the elongated tube portion 934 extends to a depth within the main chamber 902 that is approximately level with the portion of the effluent closest to the clotted mass.

A tip 936 is provided at a distal end of the elongated portion 934. The tip 936 extends from the elongated portion 934 at about a right angle. The tip includes a recess or notch 937. Two support posts 939 extend radially from the elongated portion 934 approximately at the tip 936 to contact an interior of the main chamber 902. The support posts 939 bias the tip 936 against the interior of the main chamber 902 to retain the tip 936 at a constant position in the main chamber 902. While the tip 936 contacts the interior of the main chamber 902, the notch 937 provides an opening or clearance between the interior wall of the main chamber 902 and the tip 936 to permit the passage of material through the notch 937 and into the tip 936. The tip 936 helps to maximize the amount of materials withdrawn through the elongated portion 934, particularly when the main chamber 902 is tilted to bring additional materials surrounding the tip 936 to the notch 937. The two support posts 939 and the tip 936 help center the elongated portion 934 in the main chamber 902.

The ports 908, 910, and 912 are sized to cooperate with a suitable fluid delivery or transport device, such as a syringe. For example, the first port 908 can be sized to cooperate with a reagent syringe to permit passage of reagent through the first port 908 and into the main chamber 902; the second port 910 can be sized to cooperate with a blood syringe to permit passage of blood through the second port 910 and into the main chamber 902; and the third port 912 can be sized to cooperate with a syringe to permit withdrawal of blood components, such as thrombin and other clotting factors, from within the main chamber 902.

The filter 914 can be any suitable filter for filtering materials as they are withdrawn from within the main chamber 902 through the third port 912. The filter 914 includes a polyester screen that is mounted atop the first port 908 and the second port 910. The polyester screen includes openings that are in the range of about 15 microns to about 25 microns in size. For example, the openings can be about 17 microns in size. In place of or in addition to, the filter 914, a filter similar to the filter 914 can be provided in the elongated portion 934 or at the tip 936.

The main chamber 902 further includes an activator, such as glass beads 940. The negatively charged surface of the glass beads activates clotting and the release of blood clotting factors, which form the clotted mass at the second end 906 of the main chamber 902. The glass beads 940 can be any suitable type of glass beads, such as boro-silicate beads.

An exemplary procedure for producing a clotting agent using the device of FIGS. 9A and 9B begins injection of a reagent comprising calcium chloride and ethanol into the main chamber 902 through the first port 908. After the reagent has been injected, the first port 908 is closed using the first replacement cap 922. Blood with anticoagulant is injected into the main chamber 902 through the second port 910. After the blood has been injected, the second port 910 is closed using the second replacement cap 928. Optionally, the syringes and blood separation device 900 are pre-heated to a temperature of about 25° C.

The contents of the blood component separation device 900 are mixed by repeatedly inverting the device 900, e.g. about twelve times, so as to contact the blood with the glass beads. After mixing, the device is incubated The incubation process can be at a temperature and for a duration that will permit the contents of the device 900 to be heated at about 25° C. for about 15 minutes. Upon completion of the incubation period, a clotted mass of red blood cells, blood plasma, and glass beads forms at the second end 906 of the main chamber 902. After incubation is complete, the device 900 is shaken enough to dislodge and break-up any gel that may be present. The device 900 is then placed in a suitable centrifuge and spun at about 3200 RPM's for about 15 minutes to separate thrombin from the remaining blood components. After centrifugation, an effluent of thrombin and other clotting factors separates from the clotted mass. After centrifugation is complete, the third cap 920 is removed and a suitable extraction device, such a syringe, is used to remove the effluent of thrombin and other clotting factors from within the main chamber 902 by way of the third port 912, the elongated portion 934, and the tip 936.

Delivery of the IL-1ra-rich solutions of the present technology may therefore include administration of IL-1ra, fibrinogen, thrombin, and calcium to form a fibrin matrix at the treatment site. Exogenous fibrinogen may be added to a solution of IL-1ra, for example such as bovine thrombin, preferably at 1000 U/mL. Or, the IL-1ra solution may already have an adequate amount of endogenous fibrinogen. In the case where the solution of IL-1ra and/or fibrinogen or preparation thereof includes an anticoagulant, such as ACD-A (anticoagulant citrate dextrose solution), the addition of calcium (with thrombin) to activate the fibrinogen should exceed the effective amount of any chelator in the anticoagulant.

The IL-1ra-rich solutions prepared using the present methods can provide an increased concentration of endogenous fibrinogen relative to whole blood. For example, output of the above methods employing polyacrylamide beads and the device illustrated in FIGS. 5A and 5B results in a solution rich in both IL-1ra and fibrinogen relative to whole blood. Such a device is commercially available as the Plasmax™ Plus Plasma Concentrator, from Biomet Biologics, LLC (Warsaw, Ind., USA) and includes those devices and methods of use described in U.S. Patent Application Publication No. 2006/0175268, Dorian et al., published Aug. 10, 2006; and U.S. Patent Application Publication No. 2006/0243676, Swift et al., published Nov. 2, 2006; both of which are incorporated by reference herein. This IL-1ra-rich and fibrinogen-rich solution may be used to treat the subject from which the original whole blood was derived; i.e., autologous treatment.

An IL-1ra-rich and fibrinogen-rich solution, prepared using the above methods using polyacrylamide beads with the Plasmax™ Plus Plasma Concentrator, provides a solution having about a 3-fold (3×) increase in fibrinogen concentration relative to whole blood. The fibrin matrix/clot formed from the 3× higher concentration of fibrinogen is more substantial than a fibrin clot made from baseline fibrinogen levels and is more resistant to breakdown and resorption.

Figure 10:
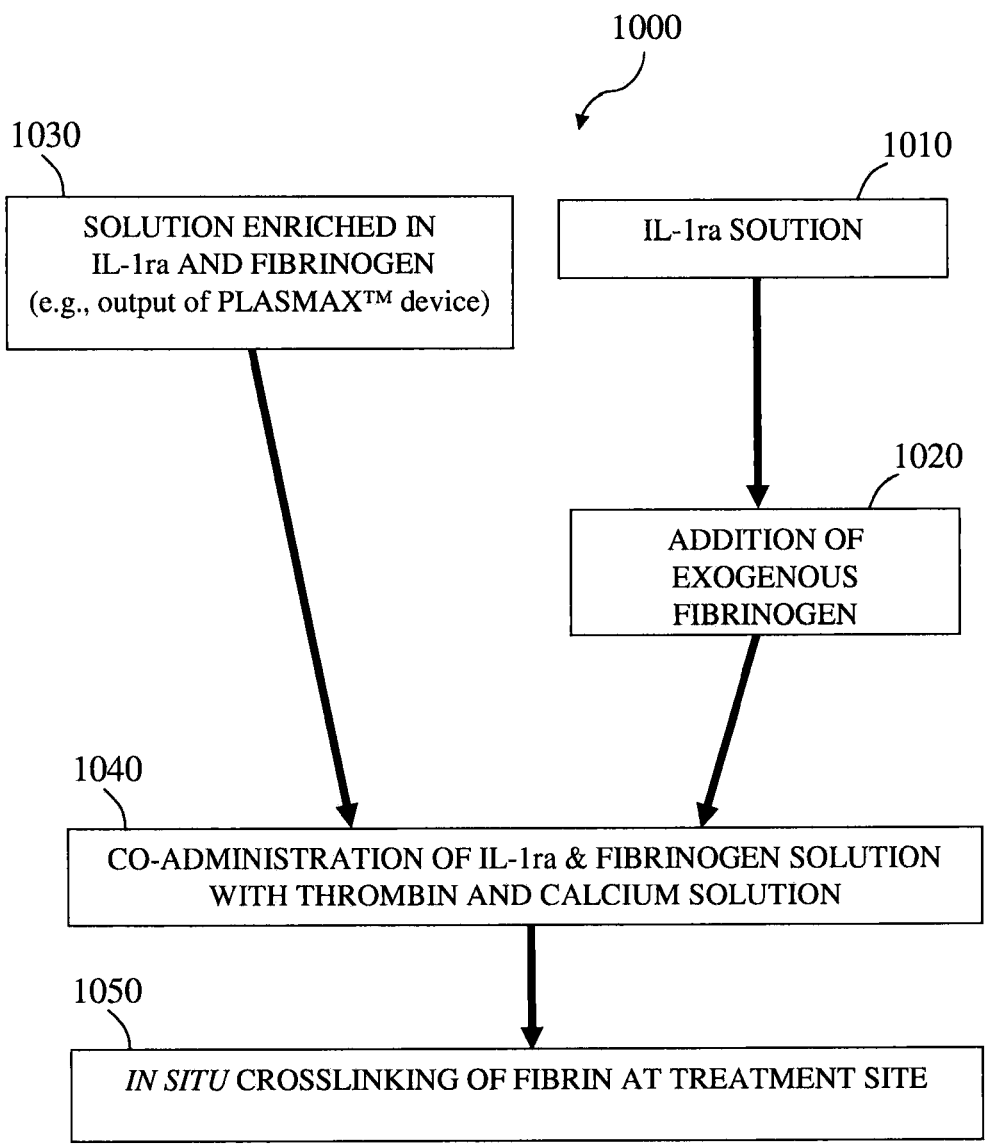
FIG. 10 is a diagrammatic illustration of a method for administering IL-1ra according to an embodiment of the present technology.

Referring to FIG. 10, a diagrammatic illustration for delivering IL-1ra 1000 is shown. At step 1010, a solution of IL-1ra (IL-1ra) is provided. The IL-1ra solution may be prepared using the methods described in the present disclosure. Exogenous fibrinogen is added to the IL-1ra (IL-1ra) solution in step 1020. The exogenous fibrinogen may be prepared from a different source than the IL-1ra solution, such as a different patient, or may be bovine in origin. Or, the exogenous fibrinogen may be prepared from different starting material than the IL-1ra solution, but still from the same source or patient. For example, the IL-1ra solution and the exogenous fibrinogen may be prepared from different blood samples taken from the same patient. Alternatively, as shown in step 1030, a solution that is enriched in both IL-1ra and fibrinogen is prepared, for example, by using liquid comprising white blood cells, polyacrylamide beads, electromagnetic field stimulation, and the Plasmax™ device, as described herein. A solution of thrombin and calcium is provided in step 1040 and is co-administered with the solution of IL-1ra to a treatment site. Thereafter, as shown in step 1050, the fibrin in the combined solutions cross-links in situ, forming a matrix at the treatment site that serves to protect, retain, and slow release of the IL-1ra.

Delivery of IL-1ra may include co-administering a first solution of IL-1ra and fibrinogen and a second solution of thrombin and calcium to a subject. In such embodiments, the first solution and second solution are kept separate until administered so that the fibrinogen does not form a fibrin matrix until after the solutions are mixed and injected into a treatment site. The solutions may be mixed just before delivery to the treatment site or may be mixed at the treatment site.

Figure 11:
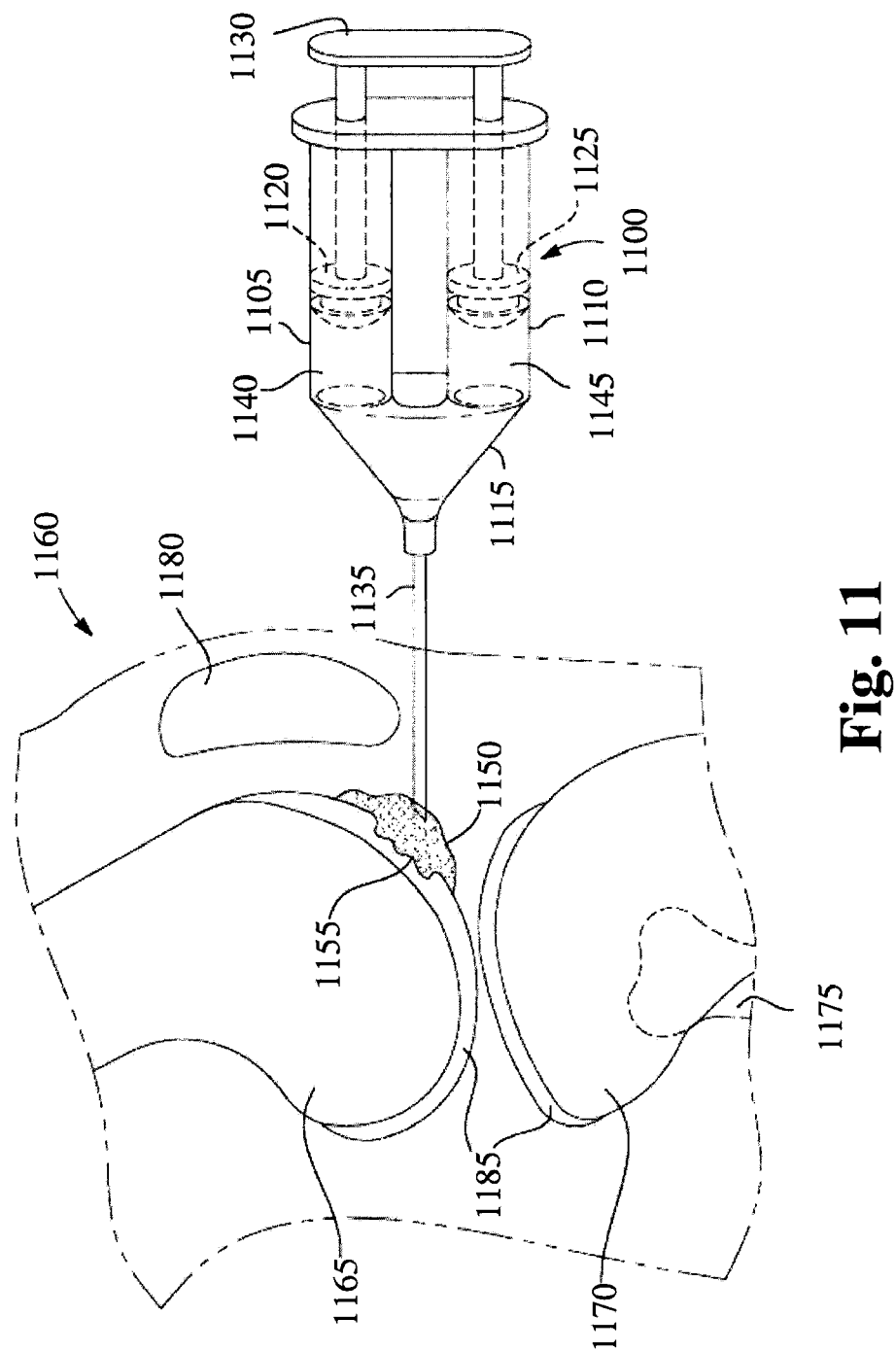
FIG. 11 is a partial cross-sectional view of a representative device administering IL-1ra according to an embodiment of the present technology.

Referring to FIG. 11, a dual syringe device 1100 may be employed in a medically appropriate procedure. The dual syringe device 1100 includes a first barrel 1105 and a second barrel 1110, both of which are connected to a mixing chamber 1115. A first plunger 1120 is inserted into the first barrel 1105 and a second plunger 1125 is inserted into the second barrel 1110. The first plunger 1120 and the second plunger 1125 are connected by a member 1130. The mixing chamber 1115 connects to a cannula 1135. The dual syringe device 1100 contains a first solution 1140 of IL-1ra and fibrinogen in the first barrel 1105, and a second solution 1145 of thrombin and calcium in the second barrel 1110. During co-administration, member 1130 is pushed toward the mixing chamber 1115 such that the contents of both the first barrel 1105 and the second barrel 1110 are pushed into the mixing chamber 1115. The mixed first solution 1140 and second solution 1145 travel through the cannula 1135 and form a fibrin-matrix 1150 at the treatment site 1155 within a patient's joint 1160.

In the embodiment shown in FIG. 11, the patient's joint 1160 is a knee joint that includes a femur 1165, a tibia 1170, a fibula 1175, a patella 1180, and cartilage 1185. It should be understood, however, that the treatment site 1155 may be in any joint of a human or animal patient, including shoulders, elbows, wrists, ankles, hips, and the spinal column. In addition, the present methods may be used to treat inflammation in sites within other tissues, such as muscle and tendon.

In some embodiments, the dual syringe device 1100 is used to pierce soft tissue of the patient's joint 1160 to administer the mixed first solution 1140 and second solution 1145. For example, the cannula 1135 may be a hollow needle such as a hypodermic needle. Alternatively, an incision may be made in the patient's joint 1160 to allow entry of the cannula 1135 so that the dual syringe device 1100 may enter the treatment site 1155.

In some embodiments, which are not shown, the dual syringe device 1100 does not have a mixing chamber 1115 and instead includes two cannulas 1135, one leading from each barrel to the treatment site 1155. In this case, the first solution 1140 and second solution 1145 travel through the separate cannulas 1135 and mix together at the treatment site 1155 to form a fibrin-matrix 1150. In some embodiments, two separate single-barreled syringe devices are employed in place of a dual syringe device.

The fibrin matrix formed in the present delivery methods can reside at the treatment site without increasing inflammation. The IL-1ra within the fibrin matrix is protected from enzymatic degradation and may bind to the fibrin matrix so that is it slowly released from the matrix over time. The methods consequently can provide sustained delivery of IL-1ra as compared to injection of IL-1ra without the fibrin-matrix carrier.

The following specific examples are provided for illustrative purposes of how to make and use the compositions and methods of this technology and, unless explicitly stated otherwise, are not intended to be a representation that given embodiments of this technology have, or have not, been made or tested.

Example 1

Characterization of Solutions Rich in IL-1ra

A solution rich in interleukin-I receptor antagonist was prepared from seven consented human providers. Blood (55 mL) was drawn into a 60 cc syringe with 5 mL of anticoagulant citrate dextrose solution A (ACD-A, Citra Anticoagulant, Inc., Braintree, Mass.). Platelet-rich plasma (PRP) was created using the GPS III platelet concentration system (800-1 003A, Biomet Biologics, Warsaw, Ind.) according to the instructions for use. The solution was generated by adding 6 mL of PRP to a modified Plasmax device containing 1 gram of polyacrylamide beads (Biomet Biologics, Warsaw, Ind.). The IL-Ira solution was removed from the Plasmax devices and was frozen at minus 50° C. for the assay. Cytokine content was assayed on a 16-plex ELISA (Searchlight Protein Array, Aushon Biosystems, Billerica, Mass.). The analytes included IL-4, IL-10, IL-11, IL-13, IL-Ira, IFN-γ, sTNF-RI, sTNF-RII, IL-1α, IL-1β, TNF-α, IL-17, IL-18, bFGF, TBF-β1, and TBF-β2.

The solution contained both anabolic (bFGF, TGF-β1, TGF-β2 (see Table 2)) and anti-inflammatory (IL-1ra, sTNF-RI, sTNF-RII, IL-4, IL-10, IL-11, IL-13, IFN-γ, (see Table 3)) cytokines without expressing large doses of catabolic cytokines (IL-1α, IL-1β, TNF-α, IL-17, IL-18 (see Table 4)). The anti-inflammatory cytokines IL-Ira and sTNF-R were all detected in ng/mL quantities, while all of the catabolic analytes were in pg/mL quantities. However, donor-to-donor variability was detected. Correlations between the catabolic cytokines IL-1 and TNF-a and anti-inflammatory analytes IL-1ra and sTNF-R were compared, but no large correlations were detected (Table 5). On average, there was about 13,260 times more IL-1ra than IL-1α and about 7,561 times more than IL-1β.

Table 2. Anabolic cytokines in the solution.

TABLE 1

| Anabolic cytokines in the solution | | | |
|---|---|---|---|
| Donor | bFGF | TGF-β1 | TGF-β2 |
| 1 | 18.5 | 1,458,008 | 153,833 |
| 2 | 10.7 | 1,137,404 | 119,545 |
| 3 | 11.9 | 585,298 | 70,544 |
| 4 | 4.9 | 1,342,442 | 162,707 |
| 5 | 20.0 | 1,579,361 | 204,670 |
| 6 | 7.7 | 1,393,746 | 170,345 |
| 7 | 13.9 | 1,474,155 | 174,502 |
| Average | 12.5 | 1,281,488 | 150,878 |
| ±SD | ±5.5 | ±336,345 | ±43,617 |

Table 3. Anti-inflammatory cytokines in the solution.

TABLE 2

| Anti-inflammatory cytokines in the solution | | | | | | | | |
|---|---|---|---|---|---|---|---|---|
| Donor | IFN-γ | IL-4 | IL-10 | IL-13 | IL-1ra | TNF-RI | TNF-RII | IL-11 |
| 1 | <0.4 | 2.1 | 0.5 | 3.5 | 9,660 | 2,728 | 2,249 | <2.0 |
| 2 | <0.4 | 1.3 | 0.3 | 2.8 | 17,477 | 5,120 | 2,900 | <2.0 |
| 3 | <0.4 | <0.8 | 0.3 | 0.1 | 23,126 | 6,247 | 2,446 | <2.0 |
| 4 | 40.4 | 59.9 | 8.9 | 19.9 | 10,458 | 4,374 | 2,612 | <2.0 |
| 5 | 30.2 | 33.9 | 23.3 | 15.8 | 13,462 | 2,763 | 1,394 | <2.0 |
| 6 | 2.6 | 23.3 | 1.4 | 25.6 | 8,813 | 2,992 | 2,716 | <2.0 |
| 7 | 0.7 | 1.2 | 0.6 | 1.8 | 11,277 | 3,330 | 1,915 | <2.0 |
| Average ± SD | 10.7 ± 17.0 | 17.5 ± 22.9 | 5.0 ± 8.7 | 9.9 ± 10.3 | 13,468 ± 5,154 | 3,936 ± 1,356 | 2,319 ± 520 | <2.0 ± 0 |

Table 4. Catabolic cytokines in the solution.

TABLE 3

| Catabolic cytokines in the solution | | | | | |
|---|---|---|---|---|---|
| Donor | IL-17 | TNF-α | IL-1α | IL-1β | IL-18 |
| 1 | 3.1 | 16.0 | <0.8 | 1.5 | 239 |
| 2 | 1.2 | <2.3 | 2.5 | 3.3 | 559 |
| 3 | 0.7 | <2.3 | 1.8 | 2.3 | 511 |
| 4 | 28.9 | 195 | 0.8 | 1.3 | 329 |
| 5 | 33.8 | 661 | 0.8 | 2.0 | 450 |
| 6 | 22.0 | 105 | 0.3 | 1.7 | 333 |
| 7 | 6.7 | <2.3 | 1.9 | 1.0 | 787 |
| Average | 13.8 | 141 | 1.3 | 1.9 | 458 |
| ±SD | ±14.1 | ±241 | ±0.8 | ±0.8 | ±183 |

Table 5. Correlation analysis.

TABLE 4

| Correlation analysis | | |
|---|---|---|
| Analytes compared | $R^2$ | Ratio |
| IL-1ra and IL-1α | 0.46 | 13,260X |
| IL-1ra and IL-1β | 0.45 | 7,561X |
| TNF-RI and TNF-α | 0.17 | 945X |
| TNF-RII and TNF-α | 0.47 | 477X |

Example 2

Figure 12:
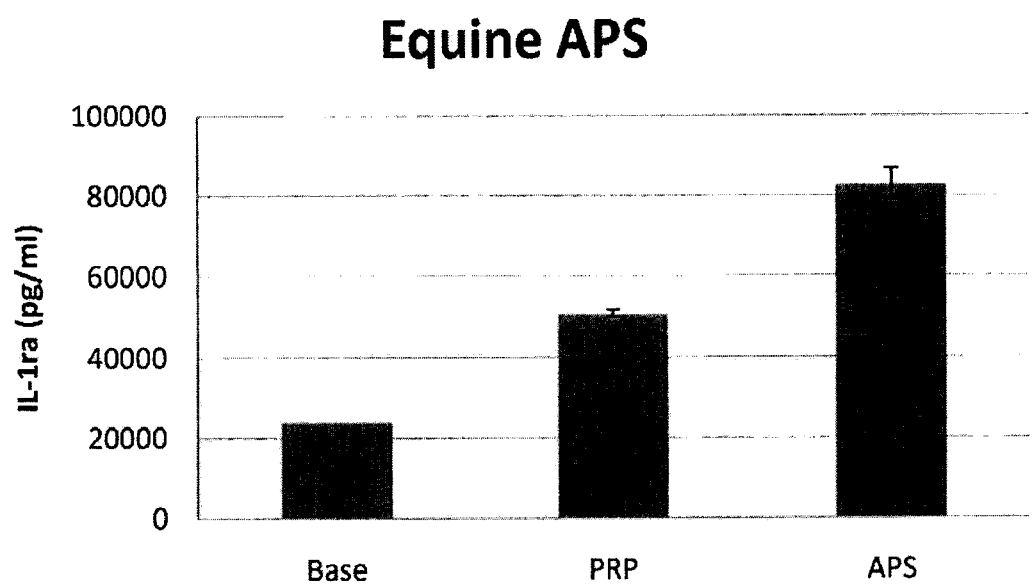
FIG. 12 is a graph showing IL-1ra concentrations in equine baseline whole blood (Base), platelet-rich plasma (PRP), and autologous protein solution (APS).

A Solution Rich in Interleukin-1 Receptor Antagonist Made from Equine Blood A solution rich in interleukin-I receptor antagonist was prepared from equine blood. Platelet-rich plasma (PRP) was created using the GPS 11I platelet concentration system (8001003A, Biomet Biologics, Warsaw, Ind.) according to the instructions for use. The solution was generated by adding 6 mL of PRP to a modified Plasmax device containing I gram of polyacrylamide beads (Biomet Biologics, Warsaw, Ind.). The IL-I ra solution was removed from the Plasmax devices and was frozen at minus 50° C. for an ELISA assay (Equine DuoSet ELISA kit, R&D Systems, Minneapolis, Minn.). Equine IL-1ra was measured in the baseline whole blood, PRP, and IL-Ira solution. The devices used were able to produce a solution rich in interleukin-I receptor antagonist (FIG. 12).

Example 3

Generation of IL-1ra from Platelet-Rich Plasma

An IL-1ra-rich solution is created as follows. Whole blood (70 mL) anticoagulated (10%) with ACD-A (Braintree, Mass., USA) is drawn from 5 healthy volunteers. A portion (10 mL) is reserved for a whole blood measurement. Platelet-rich plasma (PRP) (6 mL) is produced using the GPS® II System (Biomet Biologics, LLC, Warsaw, Ind., USA). Complete blood counts are collected for the whole blood and PRP samples following a validated procedure, as described in Woodell-May J E, Ridderman D N, Swift M J, Higgins J. "Producing Accurate Platelet Counts for Platelet Rich Plasma: Validation of a Hematology Analyzer and Preparation Techniques for Counting" *J. Craniofac. Surg.* (2005) September 16(5):749-56.

Following the PRP production, 5 mL of the PRP is added to a modified plasma concentration device (Plasmax™, Biomet Biologics LLC, Warsaw, Ind., USA) and incubated with polyacrylamide desiccating beads in the device for 24 hours at room temperature. Electromagnetic field stimulation in the form of a pulsed electromagnetic field is applied across the PRP and polyacrylamide beads using a stimulation coil. The pulse duration of the pulsed electromagnetic field is about 225 microseconds per pulse. The pulses are comprised of electromagnetic bursts in which each burst contains about 20 pulses. Each burst is repeated at a frequency of about 15 Hertz and has a duration of about 4.5 milliseconds. Following the contact with polyacrylamide beads and the stimulation with the electromagnetic field, the plasma concentration device is centrifuged to separate the serum fraction.

To analyze baseline IL-1ra levels at time zero, the whole blood and PRP samples are activated with 50 μL of thrombin and 10% $CaCl_2$ (1,000 units/mL). A blood clot is formed and incubated for 30 minutes at room temperature. Following incubation, the clot is centrifuged for 5 minutes at 3,000 rpm. Serum is collected from the clots and retained for ELISA analysis. The serum fraction from the plasma concentrator does not require activation by thrombin, and is tested directly. All samples are analyzed for IL-1ra using an ELISA kit (IL-1ra Quantikine™ Kit, R&D Systems, Minneapolis, Minn., USA).

The PRP samples result in about an eight-fold increase in platelets, about five-fold increase in total white blood cells (WBCs), about nine-fold increase in the monocyte fraction of the WBCs, and about a three-fold increase in the PMN fraction of the WBCs. The IL-1ra production in the whole blood and PRP samples is correlated most closely to the WBC concentration. The five-fold increase in the PRP is likely due to the increase in WBCs, and both the whole blood and PRP IL-1ra values can be considered baseline IL-1ra content. This is in contrast to the 195-fold increase in IL-1ra following incubation in the plasma concentrator. This plasma concentration device typically results in a 3-fold increase in plasma protein concentration due to a volume reduction caused by the desiccation process. This 3-fold decrease in volume does not account for the levels of increase seen in the amount of IL-1ra. Therefore, this level of increase indicates stimulation of WBCs to produce IL-1ra during the contact with the solid extraction material (e.g., polyacrylamide beads) and electromagnetic field stimulation.

Correlation analysis demonstrates that IL-1ra production is more closely correlated with the increase in WBCs than the platelet content. The IL-1ra levels do not correlate as closely with the monocytes population in the PRP. This is not surprising since the monocytes are not activated, and the serum is collected by thrombin activation of the plasma. However, it is possible that the monocytes, once activated in the plasma concentration device, participate in the significant production of IL-1ra seen.

Example 4

Elution of IL-1ra from a Concentrated-Plasma Matrix

Anticoagulated blood (120 cc) is collected from 5 human donors. Platelet-rich plasma (PRP) is prepared using GPS®III disposables (Biomet Biologics LLC, Warsaw, Ind., USA). PRP is loaded into modified plasma concentration devices (Plasmax™, Biomet Biologics LLC, Warsaw, Ind., USA) and processed. The output is divided into 4 groups: IL-1ra in concentrated plasma with and without thrombin activation (1000 U/mL in 1M $CaCl_2$), or cell-free IL-1ra with and without thrombin activation. IL-1ra is measured using ELISA (R&D Systems) over time.

The PRP contacts polyacrylamide beads in the Plasmax™ device while electromagnetic field stimulation is provided using a capacitively coupled electromagnetic field.

Unclotted PRP produces an average of about 50 ng over 24 hrs. The cell-free samples produce about 34 ng without changing over 24 hrs. Once clotted, the elution of IL-1ra is slowed, with only about 30% being eluted after 10 hours. Release in the cell-free samples is also delayed, but eluted 100% of available IL-1ra after 10 hours.

Example 5

Generation of IL-1ra from Adipose Tissue

Adipocytes are prepared as follows. Adipose tissue is minced into small pieces (about 1 $cm^3$) and digested in 2 mg/mL type I collagenase (Worthington Biochemical Corp., Lakewood, N.J.) under intermittent mechanical agitation in a water bath at 37° C. for 180 minutes. Digestion can be neutralized by the addition of medium or a blood-derived solution. The cell suspension is centrifuged (300×g for 7 minutes at 25° C.) followed by removal of the supernatant from the cell pellet. The pellet is then resuspended in a compatible solution to provide a liquid volume comprising adipocytes.

Alternatively, the pellet is suspended with whole blood obtained from the subject, and added to a GPS™ Platelet Concentrate System, from Biomet Biologics, Inc. (Warsaw, Ind.). Following centrifugation, the platelet-rich plasma layer, which also contains the adipocytes, is extracted from the system.

The adipocytes, optionally including platelet-rich plasma, are then combined with polyacrylamide beads and subjected to a pulsed electromagnetic field by using a pair of Helmholtz coils to stimulate production of IL-1ra. The adipocytes and polyacrylamide beads are separated from the liquid solution to obtain a solution rich in IL-1ra.

Example 6

Generation of IL-1ra from Lipoaspirate

A therapeutic composition of IL-1ra is generated from adipocytes. Isolation of human adipocytes is performed by obtaining human subcutaneous adipose tissue from lipoaspiration/liposuction procedures and digesting the tissue in collagenase type I solution (Worthington Biochemical Corp., Lakewood, N.J.) under gentle agitation for 1 hour at 37° C. The dissociated cells are filtered with 500 μm and 250 μm Nitex filters. The fraction is centrifuged at 300×g for 5 minutes. The supernatant is discarded and the cell pellet is resuspended in a compatible liquid solution, such as a blood-derived solution.

The adipocytes are combined with polyacrylamide beads in a device such as shown in FIGS. 3A and 3B. A fluid 355 containing the adipocytes is injected to the upper chamber via the inlet port 330 and mixed with the polyacrylamide beads 350. The fluid 355 and polyacrylamide beads 350 may be mixed by rotating the agitator stem 320 and the gel bead agitator 325, to help mix the fluid 355 and beads 350. The mixed fluid 355 and polyacrylamide beads 350 are then stimulated with an electromagnetic field. Electric stimulation in the form of a pulsed electromagnetic field is applied to the fluid 355 (liquid comprising adipocytes in contact with the polyacrylamide beads 350) using a stimulation coil. The pulse duration of the pulsed electromagnetic field is about 225 microseconds per pulse. The pulses are comprised of electromagnetic bursts in which each burst contains about 20 pulses. Each burst is repeated at a frequency of about 15 Hertz and has a duration of about 4.5 milliseconds. The fluid 355 is kept in contact with the polyacrylamide beads 350 and stimulated with the pulsed electromagnetic field for a desired time at a desired temperature to generate IL-1ra.

The device 300 is then centrifuged so that liquid passes to the lower chamber 310 while the polyacrylamide beads 350 are retained by a filter 345, thereby separating the polyacrylamide beads 350 from the resulting solution 360 of IL-1ra that collects in the lower chamber 310. The IL-1ra rich solution 360 may be removed from the device via outlet port 335.

The examples and other embodiments described herein are exemplary and not intended to be limiting in describing the full scope of compositions and methods of this technology. Equivalent changes, modifications and variations of specific embodiments, materials, compositions and methods may be made within the scope of the present technology, with substantially similar results.

Non-Limiting Discussion of Terminology

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

As used herein, the words "prefer" or "preferable" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components or process steps, the present technology also specifically includes embodiments consisting of, or consisting essentially of, such materials, components or processes excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, all compositional percentages are by weight of the total composition, unless otherwise specified. Disclosures of ranges are, unless specified otherwise, inclusive of endpoints and include disclosure of all distinct values and further divided ranges within the entire range. Thus, for example, a range of "from A to B" or "from about A to about B" is inclusive of A and of B. Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9,1-8, 1-3, 1-2,2-10, 2-8,2-3, 3-10, and 3-9.

What is claimed is:

1. A method for generating a solution rich in interleukin-1 receptor antagonist comprising:
    (a) contacting a liquid comprising white blood cells with a solid extraction material, wherein the solid extraction material activates the white blood cells to generate interleukin-1 receptor antagonist, and wherein the solid extraction material comprises a member selected from the group consisting of corundum, quartz, titanium, dextran, agarose, polystyrene, polyethylene, polyvinyl chloride, polypropylene, and combinations thereof;
    (b) subjecting the liquid to an electromagnetic field wherein the electromagnetic field comprises a pulsed electromagnetic field or a capacitively coupled electromagnetic field; and
    (c) separating the liquid from the solid extraction material to obtain a solution rich in interleukin-1 receptor antagonist, wherein the concentration of interleukin-1 receptor antagonist in the solution is greater than the concentration of interleukin-1 receptor antagonist in the liquid prior to contacting the liquid with the solid extraction material.

2. The method according to claim 1, wherein the contacting the liquid comprising white blood cells with the solid extraction material and the subjecting the liquid to the electromagnetic field are performed in less than 1 hour.

3. The method according to claim 1, wherein the liquid comprising white blood cells comprises whole blood, bone marrow aspirate, adipose tissue, fractions thereof, and mixtures thereof.

* * * * *